United States Patent
Li et al.

(10) Patent No.: US 11,771,375 B2
(45) Date of Patent: *Oct. 3, 2023

(54) RESPIRATION RATE DETECTION DEVICE AND BREATH DETECTION DEVICE ADOPTING MOTION DENOISING

(71) Applicant: PixArt Imaging Inc., Hsin-Chu County (TW)

(72) Inventors: Ming-Chang Li, Hsin-Chu County (TW); Ren-Hau Gu, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 1069 days.

This patent is subject to a terminal disclaimer.

(21) Appl. No.: 16/534,198

(22) Filed: Aug. 7, 2019

(65) Prior Publication Data

US 2019/0357850 A1    Nov. 28, 2019

Related U.S. Application Data

(63) Continuation-in-part of application No. 15/955,000, filed on Apr. 17, 2018, now Pat. No. 10,413,249, (Continued)

(30) Foreign Application Priority Data

Sep. 26, 2014 (TW) ................................ 103133698
Jun. 1, 2015 (TW) ................................ 104117736
(Continued)

(51) Int. Cl.
*A61B 5/00* (2006.01)
*A61B 5/024* (2006.01)

(52) U.S. Cl.
CPC .......... *A61B 5/721* (2013.01); *A61B 5/02416* (2013.01); *A61B 5/02438* (2013.01); *A61B 5/725* (2013.01); *A61B 5/7257* (2013.01)

(58) Field of Classification Search
CPC . A61B 5/721; A61B 5/02416; A61B 5/02438; A61B 5/725; A61B 5/7257; A61B 5/0816
See application file for complete search history.

(56) References Cited

U.S. PATENT DOCUMENTS 6,081,742 A    6/2000  Amano et al.
6,166,367 A   12/2000  Cho
(Continued)

FOREIGN PATENT DOCUMENTS

CN     1550204 A    12/2004
CN   101365373 A     2/2009
(Continued)

*Primary Examiner* — Hien N Nguyen
(74) *Attorney, Agent, or Firm* — WPAT, P.C

(57) ABSTRACT

A heart rate detection module including a PPG measuring device, a motion sensor and a processing unit is provided. The PPG measuring device is configured to detect a skin surface in a detection period to output a PPG signal. The motion sensor is configured to output an acceleration signal corresponding to the detection period. The processing unit is configured to respectively convert the PPG signal and the acceleration signal to first frequency domain information and second frequency domain information, determine a denoising parameter according to a maximum spectrum peak value of the second frequency domain information to denoise the first frequency domain information, and calculate a heart rate according to a maximum spectrum peak value of the denoised first frequency domain information.

18 Claims, 17 Drawing Sheets

Related U.S. Application Data which is a continuation of application No. 14/731,711, filed on Jun. 5, 2015, now Pat. No. 9,974,487, application No. 16/534,198 is a continuation-in-part of application No. 16/412,500, filed on May 15, 2019, which is a continuation-in-part of application No. 15/132,389, filed on Apr. 19, 2016, now abandoned, application No. 16/534,198 is a continuation-in-part of application No. 15/337,614, filed on Oct. 28, 2016, now abandoned.

(30) Foreign Application Priority Data

Dec. 1, 2015 (TW) .................. 104140129
Jan. 26, 2016 (TW) .................. 105102395

(56) References Cited

U.S. PATENT DOCUMENTS

| | | |
|---|---|---|
| 7,072,701 B2 | 7/2006 | Chen et al. |
| 2003/0184468 A1 | 10/2003 | Chen et al. |
| 2005/0065554 A1* | 3/2005 | KenKnight .......... A61N 1/3627 |
| | | 607/6 |
| 2006/0082490 A1 | 4/2006 | Chen et al. |
| 2009/0105556 A1 | 4/2009 | Fricke et al. |
| 2009/0306487 A1 | 12/2009 | Crowe et al. |
| 2010/0268056 A1* | 10/2010 | Picard .................. A61B 5/6804 |
| | | 600/300 |
| 2011/0071406 A1 | 3/2011 | Addison et al. |
| 2013/0072771 A1 | 3/2013 | Gu et al. |
| 2014/0073967 A1 | 3/2014 | Engelbrecht et al. |
| 2014/0221852 A1 | 8/2014 | Van Slyke et al. |
| 2014/0275854 A1* | 9/2014 | Venkatraman ....... A61B 5/1123 |
| | | 600/479 |
| 2015/0265161 A1* | 9/2015 | Hernandez .......... A61B 5/0816 |
| | | 600/483 |
| 2015/0367097 A1 | 12/2015 | Gavish |
| 2016/0220130 A1 | 8/2016 | Han et al. |
| 2016/0223514 A1 | 8/2016 | Khalak et al. |
| 2016/0235312 A1 | 8/2016 | Jeanne et al. |
| 2016/0242658 A1 | 8/2016 | Lisogurski |
| 2016/0361021 A1 | 12/2016 | Salehizadeh et al. |
| 2019/0029536 A1 | 1/2019 | Moon et al. |

FOREIGN PATENT DOCUMENTS

| | | |
|---|---|---|
| CN | 102499664 A | 6/2012 |
| JP | 5672144 B2 | 2/2015 |

* cited by examiner

| second frequency domain information I2 | | second frequency domain information I2 | first frequency domain information I1 | first frequency domain information I1 |
|---|---|---|---|---|
| second frequency index | second spectrum value | | first frequency index | first spectrum value |
| 0 | 20 | | 0 | 45 |
| 1 | 15 | | 1 | 55 |
| 2 | 10 | | 2 | 60 |
| ⋮ | ⋮ | | ⋮ | ⋮ |
| 25 | 85 | | 25 | 400 |
| ⋮ | ⋮ | denoising range 20-40 | | |
| 28 | 70 | | 28 | 420 |
| 29 | 65 | | 29 | 410 |
| 30 | 70 | | 30 | 400 |
| 31 | 65 | | 31 | 390 |
| 32 | 60 | | 32 | 400 |
| ⋮ | ⋮ | $P_{MAX}$ | ⋮ | ⋮ |
| 58 | 450 | denoising range 50-70 | 58 | 1770 |
| 59 | 455 | | 59 | 1790 |
| 60 | 460 | | 60 | 1800 |
| 61 | 450 | | 61 | 1780 |
| 62 | 445 | | 62 | 1760 |
| ⋮ | ⋮ | | ⋮ | ⋮ |
| 98 | 46 | | 98 | 870 |
| 99 | 48 | | 99 | 890 |
| 100 | 50 | $N_{HR}$ | 100 | 930 |
| 101 | 46 | | 101 | 920 |
| 102 | 44 | | 102 | 890 |
| ⋮ | ⋮ | | ⋮ | ⋮ |
| 118 | 250 | denoising range 110-130 | 118 | 1250 |
| 119 | 255 | | 119 | 1300 |
| 120 | 260 | | 120 | 1350 |
| 121 | 250 | | 121 | 1320 |
| 122 | 245 | | 122 | 1300 |
| ⋮ | ⋮ | | ⋮ | ⋮ |
| 205 | 255 | | 205 | 125 |
| ⋮ | ⋮ | | ⋮ | ⋮ |
| 1023 | 1 | | 1023 | 2 |

$R_{1/2}$ ← 30 ; half ; $R$ ← 60 ; double ; $R_2$ ← 120

$P_{MAX}$ → 460 ; $N_{HR}$ → 930 → $P_{MAX}'$

FIG. 6

| three frequency indexes of first frequency domain information I1 | | |
|---|---|---|
| N1 = 58 | N2 = 73 | N3 = 117 |

| reference index of second frequency domain information I2 |
|---|
| R = 120 |

| half of reference index and double of reference index | |
|---|---|
| R1/2 = 60 | R2 = 240 |

| denoising range | | |
|---|---|---|
| 55~65 | 115~125 | 235~245 |

FIG. 8

RESPIRATION RATE DETECTION DEVICE AND BREATH DETECTION DEVICE ADOPTING MOTION DENOISING

RELATED APPLICATIONS

The present application is a continuation-in-part application of U.S. patent application Ser. No. 15/955,000 filed on, Apr. 17, 2018, which is a continuation application of U.S. application Ser. No. 14/731,711, filed on Jun. 5, 2015, which is based on and claims priority to Taiwanese Application Number 103133698, filed Sep. 26, 2014, the disclosures of which are hereby incorporated by reference herein in their entirety. The present application is also a continuation-in-part application of U.S. patent application Ser. No. 16/412,500 filed on, May 15, 2019, which is a continuation-in-part application of U.S. application Ser. No. 15/132,389, filed on Apr. 19, 2016, which claims the priority benefit of Taiwan Patent Application Serial Number 104117736, filed on Jun. 1, 2015, the disclosures of which are hereby incorporated by reference herein in their entirety. The present application is also a continuation-in-part application of U.S. patent application Ser. No. 15/337,614 filed on, Oct. 28, 2016, which claims the priority benefit of Taiwan Patent Application Serial Number 104140129, filed on Dec. 1, 2015, and Taiwan Patent Application Serial Number 105102395, filed on Jan. 26, 2016, the full disclosures of which are incorporated herein by reference.

BACKGROUND

1. Field of the Disclosure

This disclosure generally relates to a heart rate detection module and, more particularly, to a heart rate detection module with a denoising function, a detection method thereof and a denoising method thereof.

2. Description of the Related Art

Conventional pulse oximeters utilize a noninvasive method to monitor the blood oxygenation and the heart rate of a user. A conventional pulse oximeter generally emits a red light beam (wavelength of about 660 nm) and an infrared light beam (wavelength of about 910 nm) to penetrate a part of the human body and detects an intensity variation of the penetrating light based on the feature that the oxyhemoglobin and the deoxyhemoglobin have different absorptivities in particular spectrum, e.g. referring to U.S. Pat. No. 7,072,701 and entitled "Method for spectrophotometric blood oxygenation monitoring". After the intensity variations of the penetrating light of the two wavelengths, e.g. photoplethysmography signals (PPG signals) are detected, the blood oxygenation can be calculated according to an equation: Blood oxygenation=$100\% \times [HbO_2]/([HbO_2]+[Hb])$, wherein $[HbO_2]$ is an oxyhemoglobin concentration; and $[Hb]$ is a deoxyhemoglobin concentration.

Generally, the intensity variations of the penetrating light of the two wavelengths detected by a pulse oximeter will increase and decrease with heartbeats. This is because blood vessels expand and contract with the heartbeats such that the blood volume through which the light beams pass will change to accordingly change the ratio of light energy being absorbed. Therefore, a user's heart rate is calculable according to information of the continuously-varied intensity.

However, when the part of the human body being detected has a relative movement with respect to the pulse oximeter, a disturbed signal can be detected such that it is not possible to detect a correct PPG signal. Therefore, a correct heart rate may not be obtainable under a condition of a non-static state, e.g. the pulse oximeter adapted to a portable electronic device or a wearable electronic device.

SUMMARY

Accordingly, the present disclosure provides a heart rate detection module with a denoising function, a detection method thereof and a denoising method thereof.

The present disclosure provides a respiration rate detection device including an optical sensor, a motion sensor and a processor. The optical sensor is configured to detect emergent light from a skin region in a detection period to output a PPG signal. The motion sensor is configured to output an acceleration signal corresponding to the detection period. The processor is configured to respectively convert the PPG signal and the acceleration signal to first frequency domain information, which comprises a first frequency index set and a first spectrum value set associated with the first frequency index set, and second frequency domain information, which comprises a second frequency index set and a second spectrum value set associated with the second frequency index set, identify a plurality of frequency indexes corresponding to a plurality of spectrum peak values in the first frequency domain information and the second frequency domain information, determine a reference index as a denoising parameter according to a frequency index corresponding to a maximum spectrum peak value of the second frequency domain information to denoise the first frequency domain information by removing spectrum values, which correspond to frequency indexes of the denoising parameter, from the first frequency domain information to generate denoised first frequency domain information, categorize the denoised first frequency domain information as one of a plurality of frequency zones according to predetermined categorization data, and calculate a respiration rate according to the denoised first frequency domain information within the categorized frequency zone.

The present disclosure further provides a respiration rate detection device including an optical sensor, a motion sensor and a processor. The optical sensor is configured to detect emergent light from a skin region in a detection period to output a PPG signal. The motion sensor is configured to output an acceleration signal corresponding to the detection period. The processor is configured to respectively convert the PPG signal and the acceleration signal to first frequency domain information, which comprises a first frequency index set and a first spectrum value set associated with the first frequency index set, and second frequency domain information, which comprises a second frequency index set and a second spectrum value set associated with the second frequency index set, identify a plurality of frequency indexes corresponding to a plurality of spectrum peak values in the first frequency domain information and the second frequency domain information, determine a reference index as a denoising parameter according to a frequency index corresponding to a maximum spectrum peak value of the second frequency domain information to denoise the first frequency domain information by removing spectrum values, which correspond to frequency indexes of the denoising parameter, from the first frequency domain information to generate denoised first frequency domain information, determine a set of weightings and a set of respiration rate calculation algorithms according to a signal feature of the denoised first frequency domain information, and calculate a respiration rate according to the set of weightings and the set of respiration rate calculation algorithms.

The present disclosure further provides a breath detection device including an optical sensor, a motion sensor, a band pass filter and a processor. The optical sensor is configured to detect ejected light from the skin tissues in a detection period to generate a photoplethysmography (PPG) signal. The motion sensor is configured to output an acceleration signal corresponding to the detection period. The band pass filter is configured to filter the PPG signal and the acceleration signal. The processor is configured to respectively convert the PPG signal and the acceleration signal to first frequency domain information, which comprises a first frequency index set and a first spectrum value set associated with the first frequency index set, and second frequency domain information, which comprises a second frequency index set and a second spectrum value set associated with the second frequency index set, identify a plurality of frequency indexes corresponding to a plurality of spectrum peak values in the first frequency domain information and the second frequency domain information, determine a reference index as a denoising parameter according to a frequency index corresponding to a maximum spectrum peak value of the second frequency domain information to denoise the first frequency domain information by removing spectrum values, which correspond to frequency indexes of the denoising parameter, from the first frequency domain information to generate denoised first frequency domain information, and determine a breathing signal according to the denoised first frequency domain information.

BRIEF DESCRIPTION OF THE DRAWINGS

Other objects, advantages, and novel features of the present disclosure will become more apparent from the following detailed description when taken in conjunction with the accompanying drawings.

FIG. 6 is a schematic diagram of first frequency domain information and second frequency domain information according to one embodiment of the present disclosure.

FIG. 8 is a schematic diagram of frequency indexes, a reference index and a denoising range according to one embodiment of the present disclosure.

DETAILED DESCRIPTION OF THE EMBODIMENT

It should be noted that, wherever possible, the same reference numbers will be used throughout the drawings to refer to the same or like parts.

The present disclosure provides a heart rate detection module with a denoising function and adaptable to a smart watch, a wristband, glasses, a wearable device or a portable device, but not limited thereto. In some embodiments, the wearable device or the portable device may or may not have a display function. In some embodiments, the heart rate detection module is an individual detection device and is attached to the devices in an appropriate manner while being used so as to improve the usability thereof.

Figure 1:
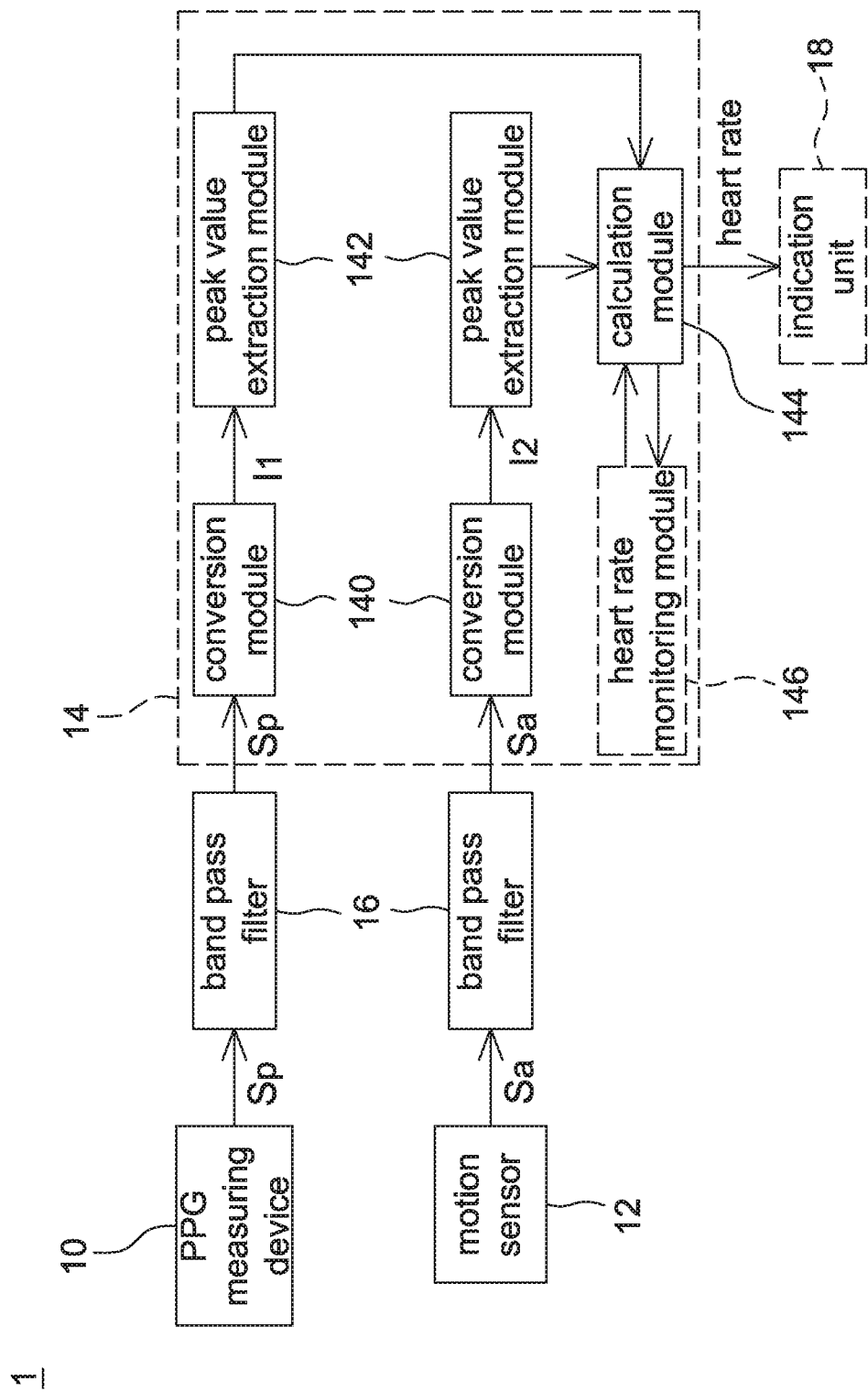
FIG. 1 is a schematic block diagram of a heart rate detection module according to one embodiment of the present disclosure.

Referring to FIG. 1, it is a schematic block diagram of a heart rate detection module 1 according to one embodiment of the present disclosure. The heart rate detection module 1 includes a photoplethysmography (PPG) measuring device 10, a motion sensor 12 and a processing unit 14, wherein the processing unit 14 includes a conversion module 140, a peak value extraction module 142 and a calculation module 144. In some embodiments, two band pass filters 16 are respectively disposed between the PPG measuring device 10 and the processing unit 14 and between the motion sensor 12 and the processing unit 14. In some embodiments, the processing unit 14 further includes a heart rate monitoring module 146 configured to record heart rates calculated by the calculation module 144. It is appreciated that a power module (not shown) is electrically connected to the heart rate detection module 1 for providing power required by the heart rate detection module 1 in operation.

The PPG measuring device 10 is configured to detect a skin surface in a detection period to output a PPG signal $S_p$. Generally speaking, the PPG measuring device 10 has a light emitting module and a sensing region. The PPG measuring device 10 is a reflective PPG measuring device or a transmissive PPG measuring device without particularly limitations. The method for the PPG measuring device 10 to generate the PPG signal $S_p$ according to detected light signals is known to the art and thus details thereof are not described herein. A location of the skin surface to be detected by the PPG measuring device 10 is not particularly limited and is determined according to an electronic device to which the heart rate detection module 1 adapted.

The motion sensor 12 is, for example, a gyroscope, an accelerometer, a G sensor or other devices configured to sense human body movement. In this embodiment, the motion sensor 12 is illustrated by taking an accelerometer as an example. The motion sensor 12 is configured to output an acceleration signal $S_a$ corresponding to the detection period of the PPG measuring device 10 so that the acceleration signal $S_a$ has a corresponding relationship with the PPG signal $S_p$. In one embodiment, the motion sensor 12 is manufactured by micro-electro-mechanical systems (MEMS) technology.

Figure 2A:
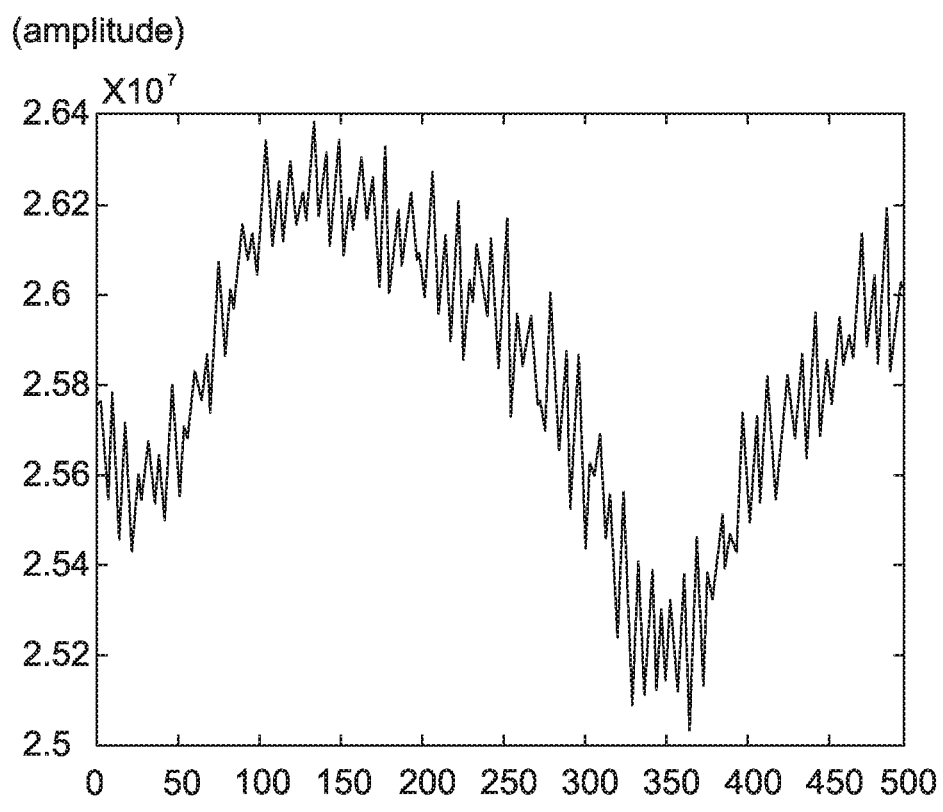
FIG. 2A is a schematic diagram of a PPG signal before being filtered according to one embodiment of the present disclosure.
Figure 2B:
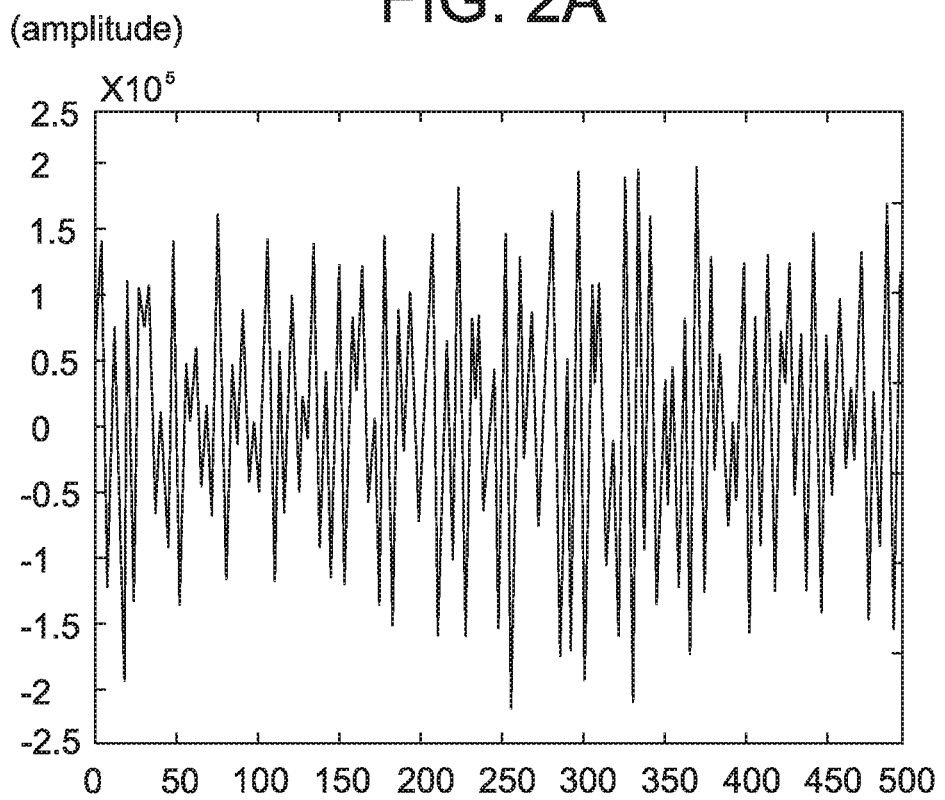
FIG. 2B is a schematic diagram of a PPG signal after being filtered according to one embodiment of the present disclosure.

In this embodiment, the heart rate detection module 1 has two band pass filters 16 respectively between the PPG measuring device 10 and the processing unit 14 and between the motion sensor 12 and the processing unit 14, and the two band pass filters 16 are respectively configured to filter the PPG signal $S_p$ and the acceleration signal $S_a$. For example, FIGS. 2A and 2B are schematic diagrams of the PPG signal $S_p$ before and after being filtered by the band pass filter 16, wherein the x-axis indicates the time and the y-axis indicates the amplitude. Generally speaking, a human heart rate is between 30 beats/min and 240 beats/min, and a signal frequency range of the human heart rate is from 0.5 Hz to 4 Hz since a heart rate of 60 beats/min corresponds to 1 Hz. Therefore, a passband of the band pass filters 16 is selected, for example, from 0.5 Hz to 4 Hz or from 0.45 Hz to 4.5 Hz so as to improve the signal quality of the PPG signal $S_p$ and the acceleration signal $S_a$ (i.e. filtering frequencies not related to the human heart rate), but not limited thereto. To simplify the description, the PPG signal and the acceleration signal after being filtered by the band pass filters 16 are also indicated by reference numbers $S_p$ and $S_a$, respectively.

It should be mentioned that although the band pass filters 16 are not included in the processing unit 14 in FIG. 1, the present disclosure is not limited thereto. In some embodiments, the band pass filters 16 are respectively disposed in the PPG measuring device 10 and the motion sensor 12. In some embodiments, the band pass filters 16 are disposed in the processing unit 14.

The processing unit 14 is, for example, a digital signal processor (DSP) or other processing devices for processing signals, and processing functions thereof are implemented by software, hardware or firmware. The processing unit 14 is configured to eliminate, according to the acceleration signal $S_a$, noise in the PPG signal $S_p$ generated by relative movements between the sensing region of the PPG measuring device 10 and the skin surface. For example, in some embodiments, the processing unit 14 converts the PPG signal $S_p$ and the acceleration signal $S_a$ respectively to first frequency domain information $I_1$ and second frequency domain information $I_2$, determines a denoising parameter according to a maximum spectrum peak value of the second frequency domain information $I_2$ to denoise the first frequency domain information $I_1$, and calculates a heart rate according to a maximum spectrum peak value of the denoised first frequency domain information.

The conversion module 140 of the processing unit 14 is configured to convert the PPG signal $S_p$ to a frequency domain PPG signal, generate a first frequency index set and a first spectrum value set associated with the first frequency index set configured as the first frequency domain information $I_1$, convert the acceleration signal $S_a$ to a frequency domain acceleration signal, and generate a second frequency index set and a second spectrum value set associated with the second frequency index set configured as the second frequency domain information $I_2$.

The peak value extraction module 142 of the processing unit 14 is configured to identify a plurality of spectrum peak values in the first frequency domain information $I_1$ and the second frequency domain information $I_2$, and output frequency indexes corresponding to the plurality of spectrum peak values to the calculation module 144.

The calculation module 144 of the processing unit 14 is configured to eliminate noise in the first frequency domain information $I_1$ according to the frequency indexes corresponding to the plurality of spectrum peak values and then calculate the heart rate (described later).

The heart rate monitoring module 146 is configured to record a variation tendency of heart rates corresponding to a plurality of the detection periods so that when the calculation module 144 is unable to directly calculate a heart rate according to the denoised first frequency domain information, the heart rate is further estimated according the variation tendency (described later).

It is appreciated that the conversion module 140, the peak value extraction module 142, the calculation module 144 and the heart rate monitoring module 146 of this embodiment indicate function blocks or program instructions inside the processing unit 14. It is appreciated that in other embodiments, the conversion module 140, the peak value extraction module 142, the calculation module 144 and the heart rate monitoring module 146 may be implemented by different processing units. It should be mentioned that two conversion modules 140 and two peak value extraction modules 142 are shown in FIG. 1, but the present disclosure is not limited thereto. The processing unit 14 may include only one conversion module 140 and only one peak value extraction module 142.

In some embodiments, the heart rate detection module 1 further includes an indication unit 18, e.g. a speaker or a display, configured to represent the heart rate through audio or images. In this case, the power module further provides power required by the indication unit 18.

In some embodiments, the indication unit 18 is not included in the heart rate detection module 1. For example, when the heart rate detection module 1 is integrated with a smart band, the indication unit 18 may be a display screen of a smart phone. In this case, the heart rate detection module 1 transmits a signal containing the heart rate information from the smart band to the smart phone in a wireless manner (e.g. Bluetooth, Wi-Fi, ZigBee or other wireless communication protocols) to show the heart rate and the variation tendency thereof in real time.

In some embodiments, the indication unit 18 is disposed in a computer system connected to a cloud system. In this case, the heart rate detection module 1 transmits a signal containing the heart rate information to the cloud system in a wireless manner for the cloud system to record the heart rate. In therapeutic applications, a medical staff may monitor the user's heart rate through the computer system.

It is appreciated that the heart rate detected by the heart rate detection module 1 may be used for different applications. In the present disclosure, it is to eliminate signal noise in the PPG signal by using the acceleration signal so as to improve the accuracy of calculating the heart rate.

Figure 3:
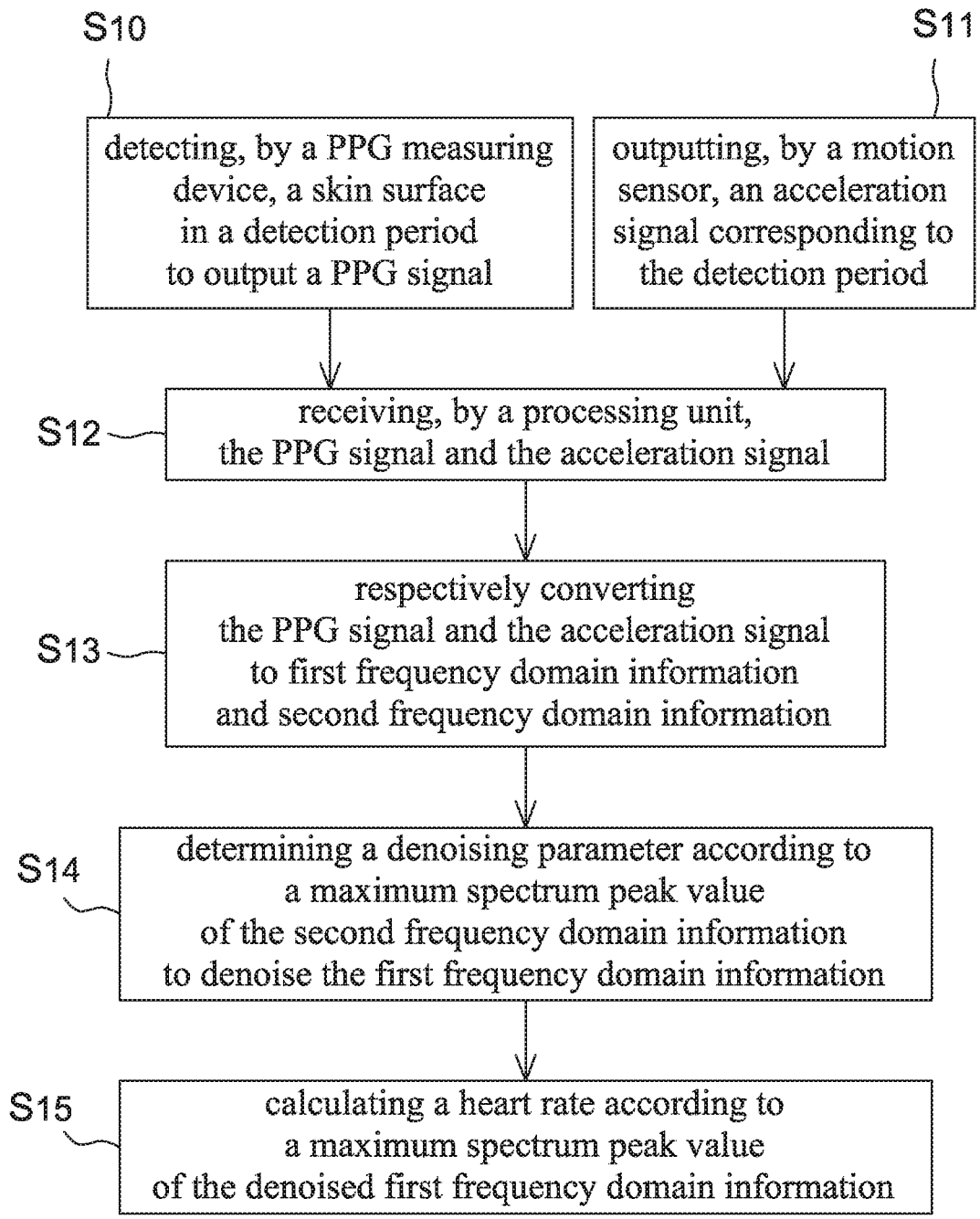
FIG. 3 is a flow chart of a heart rate detection method according to one embodiment of the present disclosure.

FIG. 3 is a flow chart of a heart rate detection method according to one embodiment of the present disclosure. The heart rate detection method includes the steps of: detecting, by a PPG measuring device, a skin surface in a detection period to output a PPG signal (Step $S_{10}$); outputting, by a motion sensor, an acceleration signal corresponding to the detection period (Step $S_{11}$); receiving, by a processing unit, the PPG signal and the acceleration signal (Step $S_{12}$); respectively converting the PPG signal and the acceleration signal to first frequency domain information and second frequency domain information (Step $S_{13}$); determining a denoising parameter according to a maximum spectrum peak value of the second frequency domain information to denoise the first frequency domain information (Step $S_{14}$); and calculating a heart rate according to a maximum spectrum peak value of the denoised first frequency domain information (Step $S_{15}$).

Figures 4A, 4B:
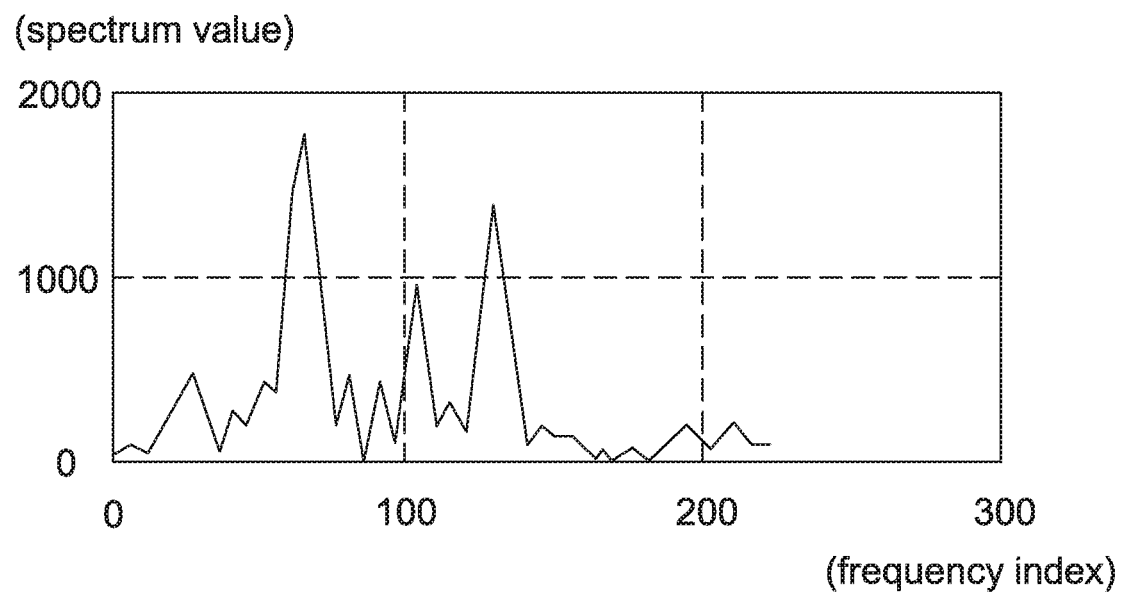
FIG. 4A is a spectrum diagram of a frequency domain PPG signal according to one embodiment of the present disclosure.
FIG. 4B is a schematic diagram of first frequency domain information corresponding to the spectrum diagram of FIG. 4A.
Figure 5A:
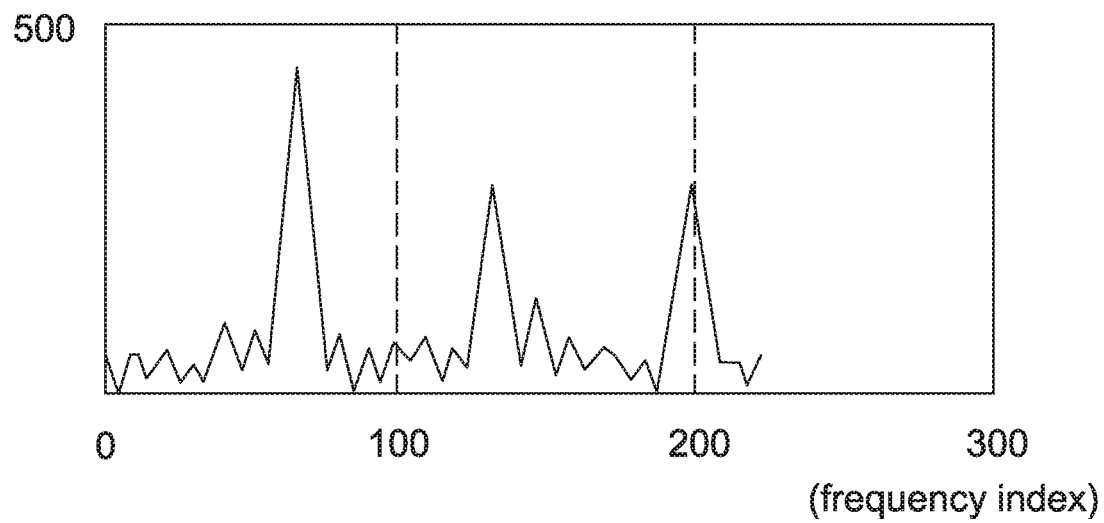
FIG. 5A is a spectrum diagram of a frequency domain acceleration signal according to one embodiment of the present disclosure.
Figure 5B:
FIG. 5B is a schematic diagram of second frequency domain information corresponding to the spectrum diagram of FIG. 5A.

Referring to FIGS. 1, 3, 4A, 4B, 5A, 5B and 6 together, details of this embodiment are described hereinafter, wherein FIGS. 4A and 4B are respectively a spectrum diagram of a frequency domain PPG signal and a schematic diagram of first frequency domain information according to one embodiment of the present disclosure, FIGS. 5A and 5B are respectively a spectrum diagram of a frequency domain acceleration signal and a schematic diagram of second frequency domain information according to one embodiment of the present disclosure, and FIG. 6 is a schematic diagram of the first frequency domain information and the second frequency domain information according to one embodiment of the present disclosure. It is appreciated that FIGS. 4A, 4B, 5A, 5B and 6 are only intended to illustrate, but not to limit the present disclosure.

Step $S_{10}$ to $S_{11}$: Firstly, a PPG measuring device 10 of a heart rate detection module 1 detects a skin surface in a detection period to output a PPG signal $S_p$. Meanwhile, a motion sensor 12 outputs an acceleration signal $S_a$ corresponding to the detection period. To simplify the description, the PPG signal $S_p$ and the acceleration signal $S_a$ in the following descriptions may indicate signals filtered by the band pass filters 16 without further indications. It should be mentioned that since the acceleration signal $S_a$ is mainly used to eliminate noise in the PPG signal $S_p$ generated by relative movements between a sensing region of the PPG measuring device 10 and the skin surface, preferably the PPG signal $S_p$ and the acceleration signal $S_a$ are related to substantially identical detection periods so that the heart rate detection module 1 may denoise information related to the PPG signal $S_p$ according to information related to the acceleration signal $S_a$ in calculating the heart rate.

Step $S_{12}$: Then, the processing unit 14 receives the PPG signal $S_p$ and the acceleration signal $S_a$ together for post processing. As shown in FIG. 1, the PPG signal $S_p$ and the acceleration signal $S_a$ are respectively inputted to a conversion module 140 of the processing unit 14.

Step $S_{13}$: The conversion module 140 of the processing unit 14 converts the PPG signal $S_p$ to a frequency domain PPG signal and generate a first frequency index set and a first spectrum value set associated with the first frequency index set, wherein each frequency index corresponds to one spectrum value. It should be mentioned that the conversion module 140 of this embodiment may use Fast Fourier Transform (FFT) to convert the PPG signal $S_p$ from time domain to frequency domain to generate the frequency domain PPG signal, but the present disclosure is not limited thereto. In other embodiments, the conversion module 140 may use Discrete Fourier Transform (DFT) or other time domain to frequency domain conversion methods (i.e. spectrum analysis) to convert the PPG signal $S_p$.

It should be mentioned that the frequency domain PPG signal is a discrete signal so that the processing unit 14 is able to perform digital signal processing accordingly. In some embodiments, when the PPG signal $S_p$ outputted by the PPG measuring device 10 is a continuous time domain signal, the conversion module 140 firstly converts the PPG signal $S_p$ to a discrete time domain signal (e.g. by sampling the PPG signal $S_p$ with a sampling frequency), and then converts the discrete time domain signal to a discrete frequency domain signal accordingly, but not limited thereto. In other embodiments, the conversion module 140 firstly converts the PPG signal $S_p$ to a continuous frequency domain signal, and then converts the continuous frequency domain signal to a discrete frequency domain signal accordingly.

As mentioned above, a signal frequency range of the human heart rate is from 0.5 Hz to 4 Hz. It is assumed that a maximum value of the signal frequency of the human heart rate is 4 Hz (corresponding to 240 beats/min), and a sampling frequency has to be larger than 8 Hz (e.g. 10 Hz or 20 Hz) so that Nyquist theorem is satisfied. In one embodiment in using FFT, the sampling frequency is 20 Hz, but not limited thereto. The sampling frequency is determined according to operating capability of the processing unit 14.

After the conversion module 140 uses FFT to convert the PPG signal $S_p$ to the frequency domain PPG signal, a spectrum diagram corresponding to the frequency domain PPG signal is generated, as shown in FIG. 4A, wherein the x-axis of the spectrum diagram indicates the frequency index of FFT and the y-axis indicates the spectrum amplitude. In this embodiment, frequency indexes and spectrum amplitudes corresponding to the frequency indexes in FIG. 4A are respectively configured as a first frequency index set and a first spectrum value set associated with the first frequency index set, i.e. first frequency domain information $I_1$, as shown in FIG. 4B.

It should be mentioned that a number of the frequency indexes of FFT is, for example, 1024 bins, but not limited thereto, wherein each of the frequency indexes corresponds to one frequency. For example, a frequency corresponding to a frequency index 256 is (20 Hz/1024)×256=5 Hz. It is appreciated that when the sampling frequency is 20 Hz and the number of the frequency indexes is 1024 bins, a frequency resolution of the first frequency domain information $I_1$ is about 20 Hz/1024=0.0195 Hz. When the sampling frequency is a fixed value and the number of the frequency indexes is higher, a frequency difference between two adjacent frequency indexes becomes smaller so that the heart rate detection module 1 has a higher sensitivity in calculating the heart rate according to the frequency indexes.

It should be mentioned that since the human heart rate is between 30 beats/min and 240 beats/min, a frequency index range corresponding to the human heart rate in the first frequency domain information $I_1$ is substantially from 25 to 205. Therefore, in some embodiments, the processing unit 14 removes (or releases) frequency indexes smaller than 25 and/or larger than 205 and the associated spectrum values for saving system resources, but not limited thereto.

Similarly, another conversion module 140 in the processing unit 14 uses the same way as converting the PPG signal $S_p$ to convert the acceleration signal $S_a$ to generate a spectrum diagram corresponding to the frequency domain acceleration signal, as shown in FIG. 5A, and generate a second frequency index set and a second spectrum value set associated with the second frequency index set configured as second frequency domain information $I_2$, as shown in FIG. 5B. In some embodiments, in the second frequency domain information $I_2$, only frequency indexes within the frequency index range (e.g. from 25 to 205) and the associated spectrum values are reserved.

Step $S_{14}$: After the second frequency domain information $I_2$ is obtained, the peak value extraction module 142 determines a reference index R according to a frequency index corresponding to a maximum spectrum peak value $P_{MAX}$ in the second frequency domain information $I_2$. For example, referring to FIG. 6, it is assumed that a maximum spectrum peak value is 460 in the second frequency domain information $I_2$. In this case, the peak value extraction module 142 identifies that the maximum spectrum peak value $P_{MAX}$ is 460 and outputs a frequency index 60 corresponding to the maximum spectrum peak value $P_{MAX}$ to the calculation module 144 configured as the reference index R. Then, the calculation module 144 calculates a half of the reference index R and a double of the reference index R. For example, when the reference index R is 60, the half of reference index $R_{1/2}$ is 30 and the double of reference index $R_2$ is 120. It is appreciated that since each of the frequency indexes indicates one frequency, a frequency corresponding to the double of reference index $R_2$ is a double of the frequency corresponding to the reference index R, and a frequency corresponding to the half of reference index $R_{1/2}$ is a half of the frequency corresponding to the reference index R.

Meanwhile, the calculation module 144 determines a denoising parameter according to the reference index R and at least one of the half of reference index $R_{1/2}$ and the double of reference index $R_2$ to denoise the first spectrum value set. For example, the denoising parameter may contain the reference index R and the half of reference index $R_{1/2}$, contain the reference index R and the double of reference index $R_2$, or contain the reference index R, the half of reference index $R_{1/2}$ and the double of reference index $R_2$. Denoising the first spectrum value set is referred to remove spectrum values in the first frequency domain information $I_1$ corresponding to the reference indexes and nearby reference indexes according to the denoising parameter obtained by the reference index R. For example, when the reference indexes $R_{1/2}$, R and $R_2$ are 30, 60 and 120 respectively, the processing unit 14 may determine, by respectively plus and minus a predetermined range to and from the reference indexes, a denoising range as 20 to 40, 50 to 70 and 110 to 130 (i.e. 30±10, 60±10 and 120±10), and remove spectrum values in the first spectrum value set associated with the denoising range configured as a method to denoise the first frequency domain information $I_1$. In some embodiments, the predetermined range is set before the shipment of the heart rate detection module 1 or in the initialization of the heart rate detection module 1.

In addition, since the second frequency domain information $I_2$ is configured for the processing unit 14 to determine the denoising parameter, in some embodiments, the processing unit 14 removes (or releases) the second frequency domain information $I_2$ for saving system resources after the calculation module 144 obtains the maximum spectrum peak value $P_{MAX}$ from the peak value extraction module 142 or after the denoising parameter is determined, but not limited thereto.

Step $S_{15}$: Finally, the calculation module 144 calculates a heart rate according to a maximum spectrum peak value of the denoised first frequency domain information. More specifically speaking, when the maximum spectrum peak value in the first frequency domain information $I_1$ is identified, the calculation module 144 removes spectrum values corresponding to the denoising range (i.e. spectrum values in the first frequency index set corresponding to the frequency indexes 20 to 40, 50 to 70 and 110 to 130). For example, after spectrum values corresponding to the denoising range are removed according to the embodiment of FIG. 6 (e.g. areas with oblique lines indicating the range of the spectrum values to be removed), the maximum spectrum peak value of the denoised first frequency domain information is determined as 930 (i.e. a denoised maximum spectrum peak value $P_{MAX}'$). The calculation module 144 then calculates a heart rate according to a frequency index (i.e. 100) corresponding to the denoised maximum spectrum peak value $P_{MAX}'$. As mentioned above, the heart rate is (20/1024)×100×60=117.19 beats/min since a heart rate of 60 beats/min corresponds to 1 Hz. Accordingly, even if the PPG measuring device 10 outputs a PPG signal containing disturbed waveform in a non-static state, the heart rate detection module 1 is still able to calculate an accurate heart rate according to the above steps.

It should be mentioned that in this embodiment, the calculation module 144 only removes (or ignores) spectrum values in the first frequency domain information $I_1$ corresponding to the denoising parameter but not to directly delete the spectrum values from a memory in identifying the maximum spectrum peak value of the first frequency domain information $I_1$ (e.g. in calculating the heart rate), but the present disclosure is not limited thereto. In some embodiments, before the step $S_{15}$ or after the denoising parameter is determined, the processing unit 14 may remove frequency indexes and spectrum values in the first frequency domain information $I_1$ corresponding to the denoising parameter from the memory in advance for saving system resources.

On the other hand, to improve the accuracy of calculating the heart rate, in some embodiments, the processing unit 14 takes a frequency index corresponding to the maximum spectrum peak value (e.g. $P_{MAX}'$) of the denoised first frequency domain information as a heart rate index $N_{HR}$ (e.g. 100). Then, a heart rate is calculated according to the heart rate index $N_{HR}$ and frequency indexes adjacent to the heart rate index $N_{HR}$. For example, referring to FIG. 6 again, when the heart rate index $N_{HR}$ is 100, the heart rate detection module 1 calculates an energy center as (99×890+100×930+101×920)/(890+930+920)=100.011 according to the heart rate index $N_{HR}$, two frequency indexes 99 and 101 adjacent to the heart rate index $N_{HR}$, and spectrum values 930, 890 and 920 respectively corresponding thereto. Then, the calculation module 144 calculates the heart rate as (20/1024)×100.011×60=117.20 beats/min according to the energy center, but not limited thereto. The calculation module 144 may calculate the heart rate according to the heart rate index and a plurality of frequency indexes (e.g. 4 or 6 frequency indexes) adjacent to the heart rate index.

Since the heart rate detection module 1 calculates one heart rate in each detection period, the heart rate detection module 1 may calculate, according to heart rates of a plurality of detection periods, a variation tendency of the heart rates of the plurality of detection periods to estimate a heart rate accordingly. In some embodiments, the processing unit 14 further includes a heart rate monitoring module 146 configured to record a variation tendency of the heart rates corresponding to a plurality of the detection periods. For example, in the embodiment of FIG. 6, after a user exercises for a period (wherein the period is, for example, longer than at least twice of the detection period), it is assumed that the denoising range is not changed and the heart rate index $N_{HR}$ varies from 100 to 110. As the calculation module 144 may ignore spectrum values corresponding to the denoising range (i.e. spectrum values corresponding to the frequency indexes 110 to 130 in the first frequency index set) when identifying the maximum spectrum peak value in the first frequency domain information $I_1$, the heart rate index $N_{HR}$ will be ignored in this case, and the calculation module 144 further estimates a current heart rate according to the variation tendency (e.g. a tendency that the heart rate index $N_{HR}$ varies from 100 to 110 during the period) recorded by the heart rate monitoring module 146.

In one aspect according to the embodiment of FIG. 6, when the heart rate index $N_{HR}$ gradually varies from 100 to 110, the calculation module 144 partially ignores spectrum values corresponding to the denoising range, e.g. ignoring spectrum values corresponding to the frequency indexes 20 to 40 and 50 to 70 but not ignoring spectrum values corresponding to the frequency indexes 110 to 130 in the first frequency index set. That is to say, the calculation module 144 takes the denoising range 110 to 130 as an invalid denoising range according to a variation of the heart rate index $N_{HR}$. In this case, the calculation module 144 calculates the heart rate according to the heart rate index $N_{HR}$ or a maximum spectrum peak value of the denoised first frequency domain information (e.g. a frequency index 120 corresponding to the spectrum value 1350 in the first spectrum value set).

Figure 7:
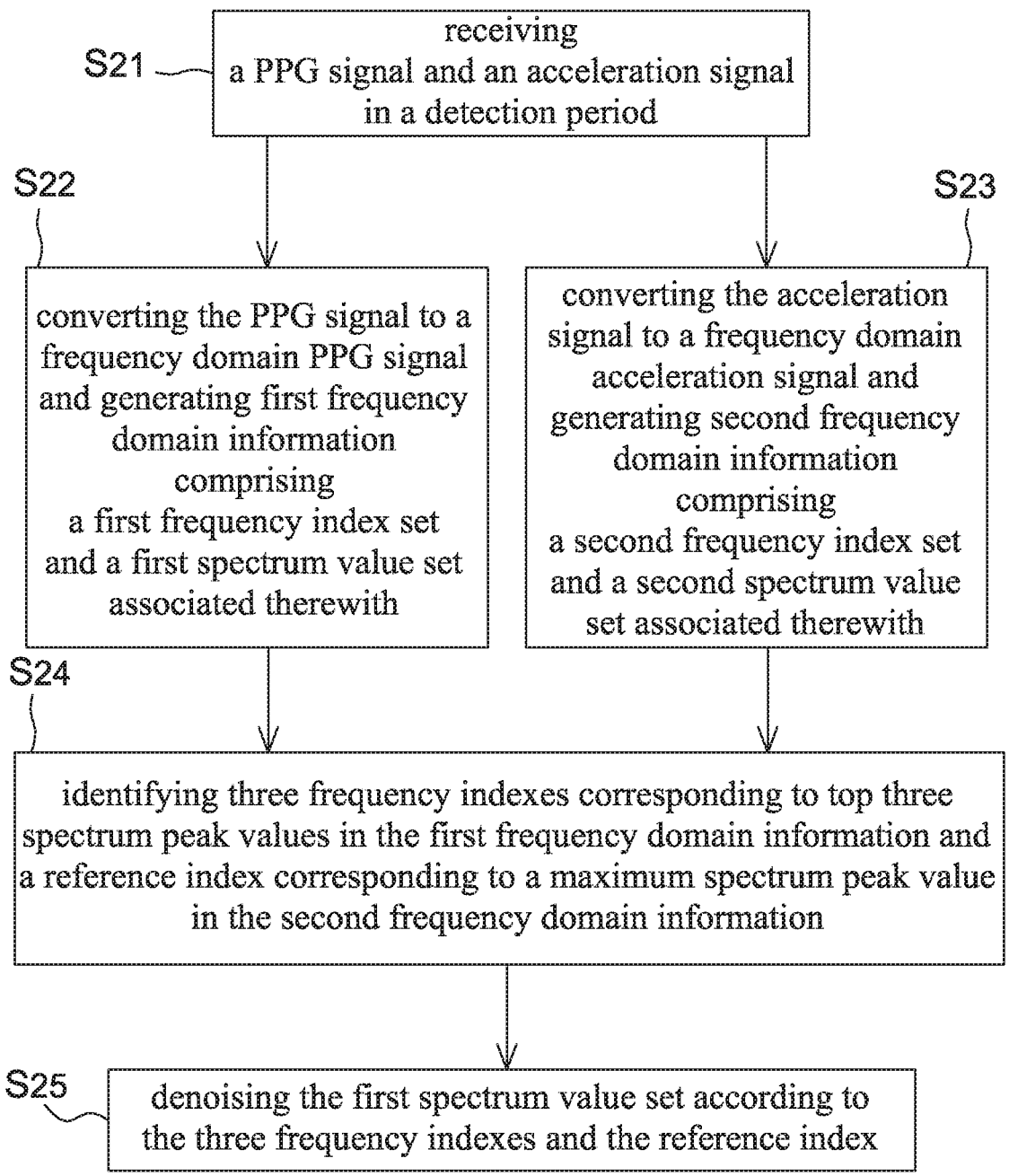
FIG. 7 is a flow chart of a denoising method according to one embodiment of the present disclosure.

FIG. 7 is a flow chart of a denoising method according to one embodiment of the present disclosure. The denoising method includes the steps of: receiving a PPG signal and an acceleration signal in a detection period (Step $S_{21}$); converting the PPG signal to a frequency domain PPG signal and generating first frequency domain information containing a first frequency index set and a first spectrum value set associated therewith (Step $S_{22}$); converting the acceleration signal to a frequency domain acceleration signal and generating a second frequency domain information containing a second frequency index set and a second spectrum value set associated therewith (Step $S_{23}$); identifying three frequency indexes corresponding to top three spectrum peak values in the first frequency domain information and a reference index corresponding to a maximum spectrum peak value in the second frequency domain information (Step $S_{24}$); and denoising the first spectrum value set according to the three frequency indexes and the reference index (Step $S_{25}$).

Referring to FIGS. 1, 6, 7 and 8 together, details of this embodiment are described hereinafter, wherein FIG. 8 is a schematic diagram of frequency indexes, a reference index and a denoising range according to one embodiment of the present disclosure.

Step $S_{21}$: Firstly, a PPG signal $S_p$ and an acceleration signal $S_a$ are received in a detection period. It is appreciated that the PPG signal $S_p$ and the acceleration signal $S_a$ are, for example, respectively outputted from a PPG measuring device 10 and a motion sensor 12, as shown in FIG. 1.

Step $S_{22}$: Then, the PPG signal $S_p$ is converted to a frequency domain PPG signal by using FFT or other time domain to frequency domain conversion methods, and first frequency domain information $I_1$ containing a first frequency index set and a first spectrum value set associated with the first frequency index set is generated, as shown in FIG. 6.

Step $S_{23}$: The acceleration signal $S_a$ is converted to a frequency domain acceleration signal by using the same method as converting the PPG signal $S_p$, and second frequency domain information $I_2$ containing a second frequency index set and a second spectrum value set associated with the second frequency index set is generated. In this embodiment, since the heart rate detection module 1 includes two independent conversion modules 140, the steps $S_{23}$ and $S_{22}$ may be performed at the same time, but not limited thereto.

It is appreciated that a processing unit 14 may reserve required information of frequency indexes and spectrum values in the first frequency domain information $I_1$ and the second frequency domain information $I_2$ and store in a memory unit, e.g. only reserving the frequency indexes 0 to 225 and spectrum values associated therewith, but not limited thereto.

Step $S_{24}$: After the first frequency domain information $I_1$ and the second frequency domain information $I_2$ are obtained, the processing unit 14 identifies three frequency indexes $N_1$, $N_2$ and $N_3$ corresponding to top three spectrum peak values in the first frequency domain information $I_1$ and a reference index R corresponding to a maximum spectrum peak value in the second frequency domain information $I_2$. For example, the three frequency indexes $N_1$, $N_2$ and $N_3$ corresponding to the top three spectrum peak values in the first frequency domain information $I_1$ are respectively 58, 73 and 117, and the reference index R corresponding to the maximum spectrum peak value in the second frequency domain information $I_2$ is 120, as shown in FIG. 8.

Step $S_{25}$: Finally, the processing unit 14 calculates a half of frequency index $R_{1/2}$ and/or a double of frequency index $R_2$ as 60 and 240, and determines a denoising range, wherein the denoising range is, for example, determined by plus and minus 5 to and from the reference indexes $R_{1/2}$, R and $R_2$, as 55 to 65, 115 to 125 and 235 to 245, as shown in FIG. 8. Accordingly, the processing unit 14 denoises the frequency domain PPG signal according to the denoising range determined by the three frequency indexes $N_1$ to $N_3$ and the reference index R.

As mentioned above, in a non-static state, the PPG measuring device 10 may output incorrect PPG signals so that the processing unit 14 may not directly calculate a correct heart rate according to the PPG signal. Therefore, after the denoising range is determined through the steps $S_{21}$ to $S_{25}$ of this embodiment, spectrum values in the first frequency domain information $I_1$ associated with frequency indexes within the denoising range may be noise, and the processing unit 14 may remove frequency indexes in the first frequency domain information $I_1$ within the denoising range or spectrum values associated with the frequency indexes so as to denoise the first frequency domain information $I_1$.

In one application, the denoising method is adapted to, for example, calculate a heart rate. Referring to FIG. 8 again, when the frequency indexes $N_1$ and $N_3$ of the first frequency domain information $I_1$ is in the denoising range (i.e. 58 and 117 are respectively between 55 to 65 and 115 to 125) and the frequency index $N_2$ is not in the denoising range, the processing unit 14 may determine a heart rate index $N_{HR}$ as 73 (i.e. the frequency index $N_2$) among the three frequency indexes $N_1$, $N_2$ and $N_3$ according to the denoising range. Then, the processing unit 14 calculates a heart rate according to the heart rate index $N_{HR}$. For example, the heart rate is (20/1024)×73×60=85.55 beats/min. In some embodiment, the processing unit 14 calculates a heart rate according to the heart rate index $N_{HR}$ and frequency indexes adjacent to the heart rate index $N_{HR}$. The calculation method thereof is described above and thus details thereof are not repeated herein.

It should be mentioned that the denoising range is based on the frequency indexes $N_1$ to $N_3$ and generated by plus and minus a predetermined range (i.e. 5) to and from the frequency indexes $N_1$ to $N_3$, wherein the predetermined range may or may not be related to a sampling frequency of the conversion module 140 and a number of the frequency indexes. As mentioned above, a frequency resolution is determined by the sampling frequency and the number of the frequency indexes. In some embodiments, the predetermined range is inversely correlated with the frequency resolution, but not limited thereto.

In some embodiments, the processing unit 14 further determines two residual indexes as 58 and 117 (i.e. the frequency indexes $N_1$ and $N_3$) among the three frequency indexes $N_1$ to $N_3$ according to the denoising range. It is assumed that the denoising range and the residual indexes $N_1$ and $N_3$ are not changed. After a user exercises for a period, since the user's heart rate rises, the frequency index $N_2$ associated with the heart rate is gradually approaching the frequency index $N_3$ so that the frequency index $N_2$ falls into the denoising range (i.e. the frequency indexes 115 to 125). In this case, the processing unit 14 may not determine the heart rate index $N_{HR}$ among the three frequency indexes $N_1$ to $N_3$ according to the denoising range. Therefore, when a difference value between the heart rate index $N_{HR}$ (e.g. the frequency index $N_2$) and one of the residual indexes (e.g. the frequency indexes $N_1$ or $N_3$) is smaller than a threshold, the processing unit 14 may estimate a heart rate according to a variation tendency of the heart rate indexes $N_{HR}$ corresponding to a plurality of the detection periods.

For example, it is assumed that the threshold is 10 and the heart rate index $N_{HR}$ varies from 73 to 110 after the period. In this case, a difference value between the heart rate index $N_{HR}$ and the residual index 117 (i.e. the frequency index $N_3$) is 7, which is smaller than the threshold, and the processing unit 14 then estimates a heart rate according to the variation tendency of the heart rate indexes $N_{HR}$ corresponding to a plurality of the detection periods, wherein the heart rate calculation method according to the variation tendency and the frequency indexes is described above, and thus details thereof are not repeated herein.

In the above embodiments, the PPG signal $S_p$ of the PPG measuring device 10 and the acceleration signal $S_a$ of the motion sensor 12 are not only configured to calculate a heart rate. The processing unit 14 further calculates a physiology state and exercise data (e.g. step counting, running/riding velocity calculation, and sport time recording) according to the PPG signal $S_p$ and the acceleration signal $S_a$ according to different applications.

In addition to denoise the PPG signal by using the acceleration signal to obtain denoised frequency domain information for calculating a heart rate as mentioned above, in another embodiment, the above denoising method is further applicable to denoise the PPG signal by using the acceleration signal to obtain denoised frequency domain information for calculating a respiration rate.

Figure 9:
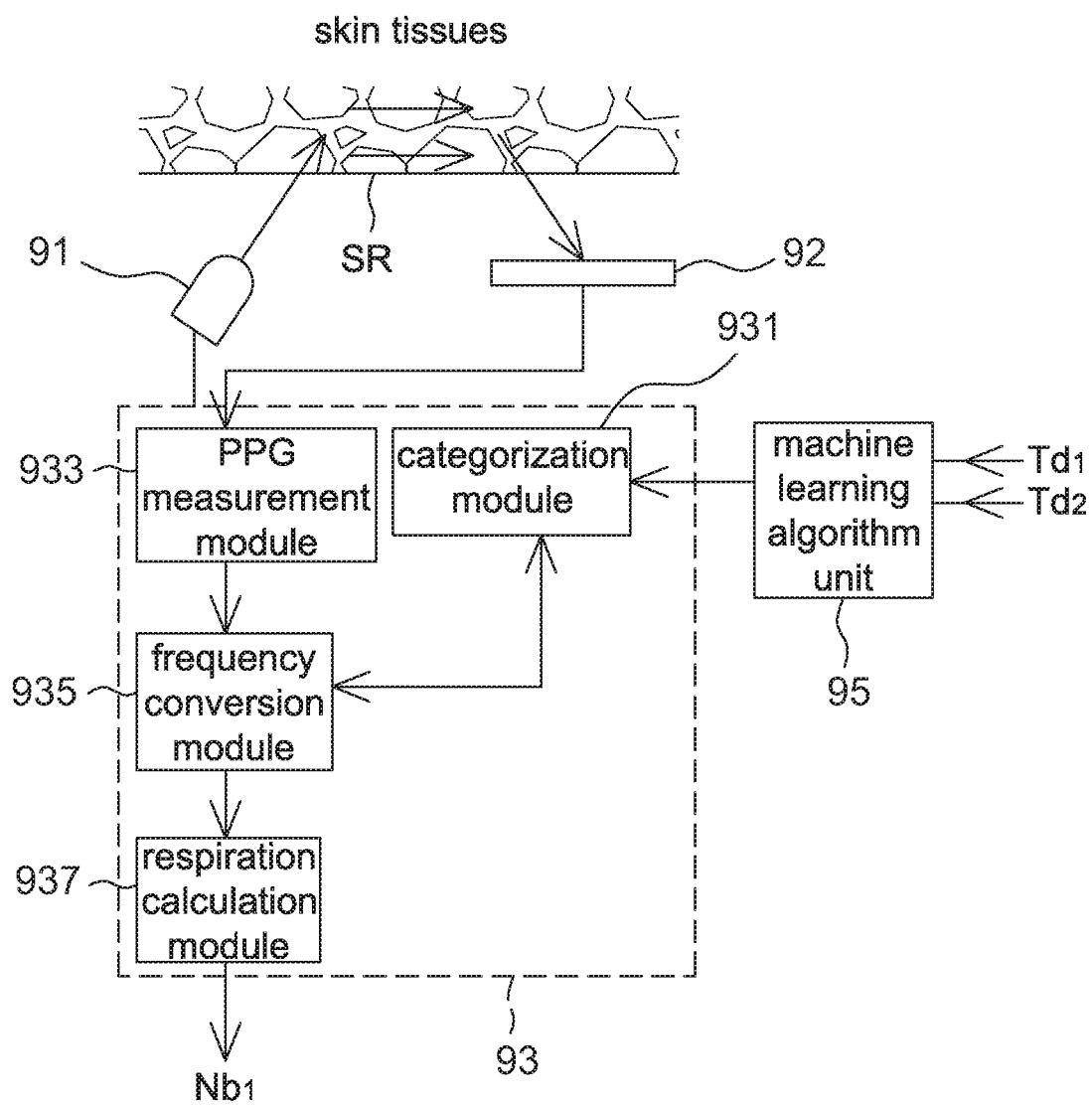
FIG. 9 is a schematic block diagram of a respiration rate detection device according to one embodiment of the present disclosure.

Referring to FIG. 9, it is a schematic block diagram of a respiration rate detection device 900 according to one embodiment of the present disclosure. The respiration rate detection device 900 categorizes currently detected photoplethysmography signals (or PPG signals) according to predetermined categorization data so as to remove the noise interference in a part of frequency zones thereby increasing the detection accuracy.

The respiration rate detection device 900 includes a light source 91, an optical sensor 92 and a processor 93. The processor 93 is further connected to a motion sensor (e.g., 12 shown in FIG. 1) to receive an acceleration signal. The respiration rate detection device 900 further includes at least one band pass filter to filter the PPG signal and the acceleration signal.

The light source 91 is selected from a coherent light source, a partially coherent light source or a non-coherent light source without particular limitations, e.g., a light emitting diode or a laser diode. The light source 91 provides light to illuminate a skin region SR. The light enters skin tissues under the skin region SR and then emerges from the skin region SR after propagating inside the skin tissues for a distance. In some embodiments, an illumination wavelength of the light source 91 is selected from those used in conventional pulse oximeters. In other embodiments, an illumination wavelength of the light source 91 is selected from 300 nm to 940 nm. It should be mentioned that, although FIG. 9 shows only one light source 91, it is only intended to illustrate but not to limit the present disclosure. In some embodiments, if the respiration rate detection device 900 is also used for detecting an oxygen saturation, two light sources respectively illuminating red light and infrared light are used. In other embodiments, if the respiration rate detection device 900 also has a calibration function, three light sources respectively illuminating green light, red light and infrared light are used, wherein the green light PPG signal is used to determine a filter parameter for filtering the red light PPG signal and the infrared light PPG signal.

The optical sensor 92 detects light emergent from the skin region SR and outputs an intensity variation signal. In some embodiments, the optical sensor 92 is a photodiode and the intensity variation signal outputted from the photodiode is used as the PPG signal. In some embodiments, the optical sensor 92 is an image sensor which has a pixel array including a plurality of pixels. Each pixel of the pixel array respectively outputs an intensity signal within a frame and the processor 93 further calculates a sum of the intensity signals outputted from a plurality of pixels within the frame, wherein a variation of the sum of the intensity signals with time is used as the PPG signal. In some embodiments, an intensity variation signal outputted by each pixel of the pixel array is used as the PPG signal, i.e. the pixel array outputting a plurality of intensity variation signals. In addition, in some embodiments when the optical sensor 92 is an image sensor, it is preferably an active image sensor, e.g., a CMOS image sensor. In the active image sensor, a window of interest is determined according to an actual intensity distribution detected by the pixel array thereof, wherein the processor 93 processes pixel data only within the window of interest but ignores pixel data outside the window of interest so as to improve the practicability thereof.

The processor 93 is, for example, a digital signal processor (DSP), a microcontroller (MCU) or a central processor (CPU) for receiving and post-processing the intensity variation signal outputted from the optical sensor 92 and the acceleration signal outputted from a motion sensor 12. In this embodiment, the processor 93 converts the intensity variation signal to frequency domain data, categorizes the frequency domain data into one of a plurality of frequency zones according to predetermined categorization data, and calculates a respiration rate according to the frequency domain data of the categorized frequency zone.

To denoise the PPG signal at first, the processor 93 respectively converts the PPG signal and the acceleration signal to first frequency domain information, which comprises a first frequency index set and a first spectrum value set associated with the first frequency index set (e.g., referring to FIGS. 4A and 4B), and second frequency domain information, which comprises a second frequency index set and a second spectrum value set associated with the second frequency index set (e.g., referring to FIGS. 5A and 5B). Then, the processor 93 identifies a plurality of frequency indexes corresponding to a plurality of spectrum peak values in the first frequency domain information and the second frequency domain information. The processor 93 further determines a reference index as a denoising parameter according to a frequency index corresponding to a maximum spectrum peak value of the second frequency domain information to denoise the first frequency domain information by removing spectrum values, which correspond to frequency indexes of the denoising parameter, from the first frequency domain information to generate denoised first frequency domain information. Details of these operations performed by the processor 93 have been described above, e.g., referring to FIGS. 4A-4B, 5A-5B, 6 and the corresponding descriptions thereof.

The processor 93 includes, for example, a categorization module 931, a PPG measurement module 933, a frequency conversion module 935 and a respiration calculation module 937. It should be mentioned that although FIG. 9 shows functions performed by the processor 93 as different functional blocks, it is only intended to illustrate but not to limit the present disclosure. The functions performed by the categorization module 931, the PPG measurement module 933, the frequency conversion module 935 and the respiration calculation module 937 are all considered to be performed by the processor 93 and implemented by software, hardware or a combination thereof without particular limitations.

Figure 10A:
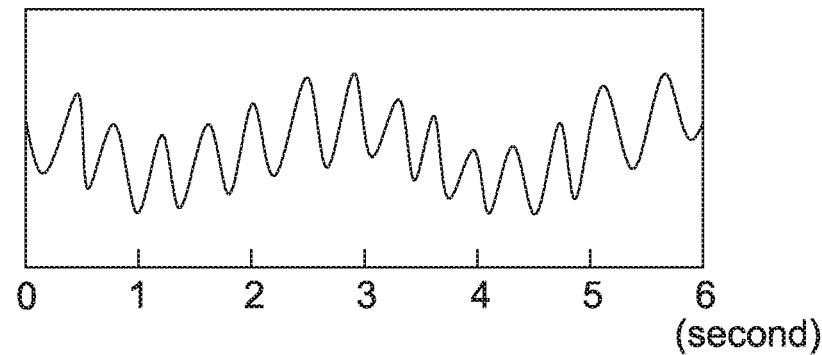
FIG. 10A is a schematic diagram of an intensity variation signal generated by a respiration rate detection device according to one embodiment of the present disclosure.
Figure 10B:
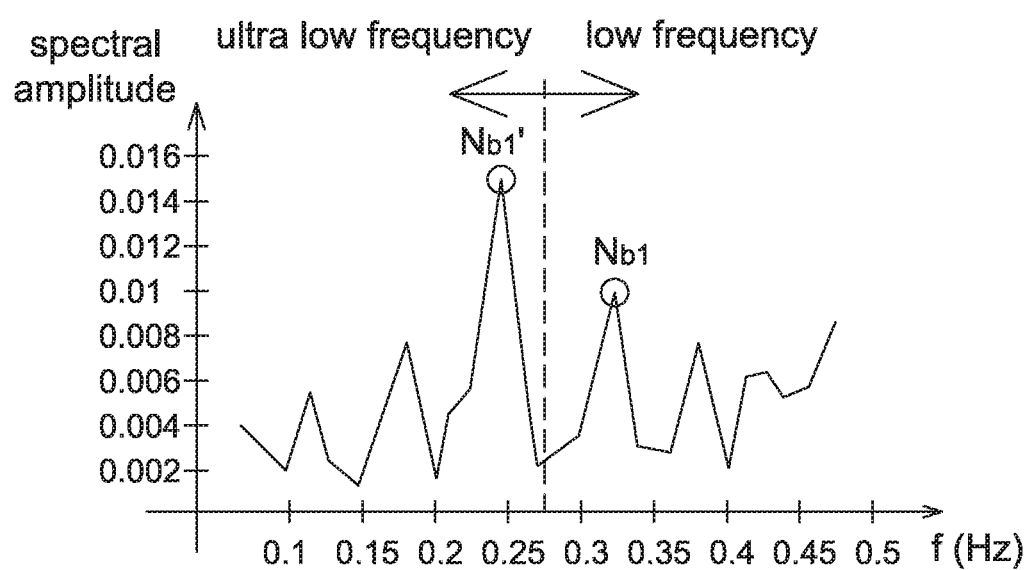
FIG. 10B is a schematic diagram of frequency domain data generated by a respiration rate detection device according to one embodiment of the present disclosure.

Referring to FIGS. 9 and 10A-10B, FIG. 10A is a schematic diagram of an intensity variation signal (or PPG signal) generated by a respiration rate detection device according to an embodiment of the present disclosure, and FIG. 10B is a schematic diagram of frequency domain data generated by a respiration rate detection device according to an embodiment of the present disclosure.

The PPG measurement module 933 receives the intensity variation signal from the optical sensor 92 and continuously acquires intensity signals within a time interval, e.g., 5 to 10 seconds, to be used as the PPG signal. For example, FIG. 10A shows the intensity variation signal within a time interval of 6 seconds to be used as the PPG signal. As the optical sensor 92 sequentially outputs intensity signals at a sample rate (or frame rate), the time intervals may or may not be overlapped with one another in time. For example, the PPG measurement module 933 takes the intensity variation signal between 1 to 7 seconds as a next PPG signal or takes the intensity variation signal between 7 to 13 seconds as a next PPG signal, and so on.

When the optical sensor 92 is a photodiode, the PPG measurement module 933 directly retrieves the intensity variation signal being outputted within a time interval as the PPG signal, wherein the PPG measurement module 933 does not perform any processing on the intensity variation signal or performs the pre-processing such as filtering or amplifying on the intensity variation signal. When the optical sensor 92 is an image sensor, the PPG measurement module 933 calculates a sum of intensity signals of at least a part of pixel data (e.g. pixel data within a window of interest) of every frame outputted by the pixel array, and continuously retrieves the sum of intensity signals within a time interval, e.g., 5 to 10 seconds, as the PPG signal as shown in FIG. 10A. In other embodiments, when the optical sensor 92 is an image sensor, the image sensor itself has the function of calculating the sum of intensity signals (e.g., implemented by circuit). In this case, the PPG measurement module 933 retrieves the sum of intensity signals within a time interval, e.g., 5 to 10 seconds, as the PPG signal. In this case, the PPG measurement module 933 does not perform any processing on the sum of intensity signals or performs the pre-processing such as filtering or amplifying on the sum of intensity signals. It should be mentioned that although FIG. 10A shows the intensity variation signal within 6 seconds being used as the PPG signal, it is only intended to illustrate but not to limit the present disclosure.

In one aspect, the light source 91, the optical sensor 92 and the PPG measurement module 933 in FIG. 9 form the PPG measuring device 10 in FIG. 1. The processor 93 includes the categorization module 931, the frequency conversion module 935, and the respiration calculation module 937.

The frequency conversion module 935 converts the intensity variation signal (or PPG signal) into frequency domain data as shown in FIG. 10B, wherein the frequency conversion is selected from, for example, the fast Fourier transform (FFT) or discrete Fourier transform (DFT) without particular limitations.

To denoise the PPG signal, the frequency conversion module 935 respectively converts the PPG signal from the PPG measurement module 933 and the acceleration signal from the motion sensor 12 to the first frequency domain information and the second frequency domain information as shown in FIGS. 4A-4B, 5A-5B and 6. Or the processor 93 has two conversion modules (as shown in FIG. 1) respectively converts the PPG signal to the first frequency domain information and converts the acceleration signal to the second frequency domain information. Details thereof have been described above, and thus are not repeated herein.

As shown in FIG. 10B, if there is no ultra low frequency noise, the maximum spectral amplitude should appear at a position Nb1 in the frequency domain data (or denoised first frequency domain information if denoising by the acceleration signal is performed). However, when ultra low frequency noises exist, another maximum spectral amplitude at a position Nb1' could exist in the frequency domain data (or the denoised first frequency domain information) to lead to a misidentification. Accordingly, the frequency conversion module 935 further sends the frequency domain data (or the denoised first frequency domain information) to the categorization module 931 to be compared with predetermined categorization data therein. The categorization module 931 categorizes the frequency domain data (or the denoised first frequency domain information) as one of a plurality of frequency zones, e.g., an ultra low frequency zone or a low frequency zone shown in FIG. 10B. In some embodiments, the categorization module 931 separates two frequency zones by an isolation frequency, wherein the isolation frequency is selected from a frequency range between 0.15 Hz and 0.25 Hz, but not limited thereto. It is appreciated that when the processor 93 separates more than two frequency zones, the isolation frequencies are selected from more than two frequency ranges.

In the present disclosure, the predetermined categorization data is previously built up by a machine learning algorithm, wherein the machine learning algorithm is implemented by, e.g., the neural network, support vector machine, random forest and so on without particular limitations. As shown in FIG. 9, a machine learning algorithm unit 95 previously receives a plurality of ultra low frequency learning data Td1 and low frequency learning data Td2 for learning so as to recognize data characteristics of different frequency zones, wherein the ultra low frequency learning data Td1 and the low frequency learning data Td2 are the frequency domain data obtained from the categorized (e.g., categorized ultra low frequency data or categorized low frequency data) PPG signal previously converted by the frequency conversion module 935. It is appreciated that when there are more frequency zones to be categorized (i.e. not limited to the ultra low frequency zone or low frequency zone), more types of the learning data (i.e. frequency domain data) are required. It should be mentioned that although FIG. 9 shows that the machine learning algorithm unit 95 is outside of the processor 93, e.g., in an external host or an external computer system, the present disclosure is not limited thereto. In other embodiments, the machine learning algorithm unit 95 is included inside the processor 93.

Finally, the respiration calculation module 937 calculates a respiration rate Nb1 according to the frequency domain data (or the denoised first frequency domain information) of the categorized frequency zone. For example, the respiration calculation module 937 takes a frequency corresponding to a maximum spectral amplitude in the categorized frequency zone as a respiration frequency (respiration rate). Referring to FIG. 10B, when the categorization module 931 categorizes current frequency domain data (or current denoised first frequency domain information) into the low frequency zone, the respiration calculation module 937 takes a frequency corresponding to the maximum spectral amplitude Nb1 therein as a current respiration rate, which is then outputted; when the categorization module 931 categorizes current frequency data (or current denoised first frequency domain information) as the ultra low frequency zone, the respiration calculation module 937 takes a frequency corresponding to the maximum spectral amplitude Nb1' therein as a current respiration rate, which is then outputted.

In this embodiment, the processor 93 ignores the frequency domain data (or the denoised first frequency domain information) outside the categorized frequency zone. For example, when the frequency domain data is categorized as the low frequency zone, the frequency domain data in the ultra low frequency zone is ignored; whereas, when the frequency domain data is categorized as the ultra low frequency zone, the frequency domain data in the low frequency zone is ignored. In addition, the operation of embodiments having more frequency zones is similar. It is possible to implement the ignoring as below.

In one embodiment, the frequency conversion module 935 provides current frequency domain data (or current denoised first frequency domain information) to the categorization module 931 to be compared with predetermined categorization data therein and categorized. The categorization module 931 informs the frequency conversion module 935 of the categorized result to allow the frequency conversion module 935 to provide the frequency domain data (or the denoised first frequency domain information) only in the categorized frequency zone to the respiration calculation module 937. Accordingly, the respiration calculation module 937 will not process the frequency domain data outside the categorized frequency zone.

In another embodiment, the frequency conversion module 935 provides all current frequency domain data (or current denoised first frequency domain information) to the respiration calculation module 937, and the categorization module 931 provides categorization information to the respiration calculation module 937. Accordingly, when a current respiration rate obtained by the respiration calculation module 937 is within a categorized frequency zone, the current respiration rate is outputted; whereas, when the current respiration rate obtained by the respiration calculation module 937 is not within the categorized frequency zone, a frequency corresponding to a next maximum spectral amplitude is calculated and confirmed with the categorized frequency zone till a current respiration rate within the categorized frequency zone is obtained and the current respiration rate within the categorized frequency zone is then outputted. Or the respiration calculation module 937 calculates the current respiration rate according to the frequency domain data (or the denoised first frequency domain information) only within a categorized frequency zone but ignores the frequency domain data outside the categorized frequency zone.

Figure 11:
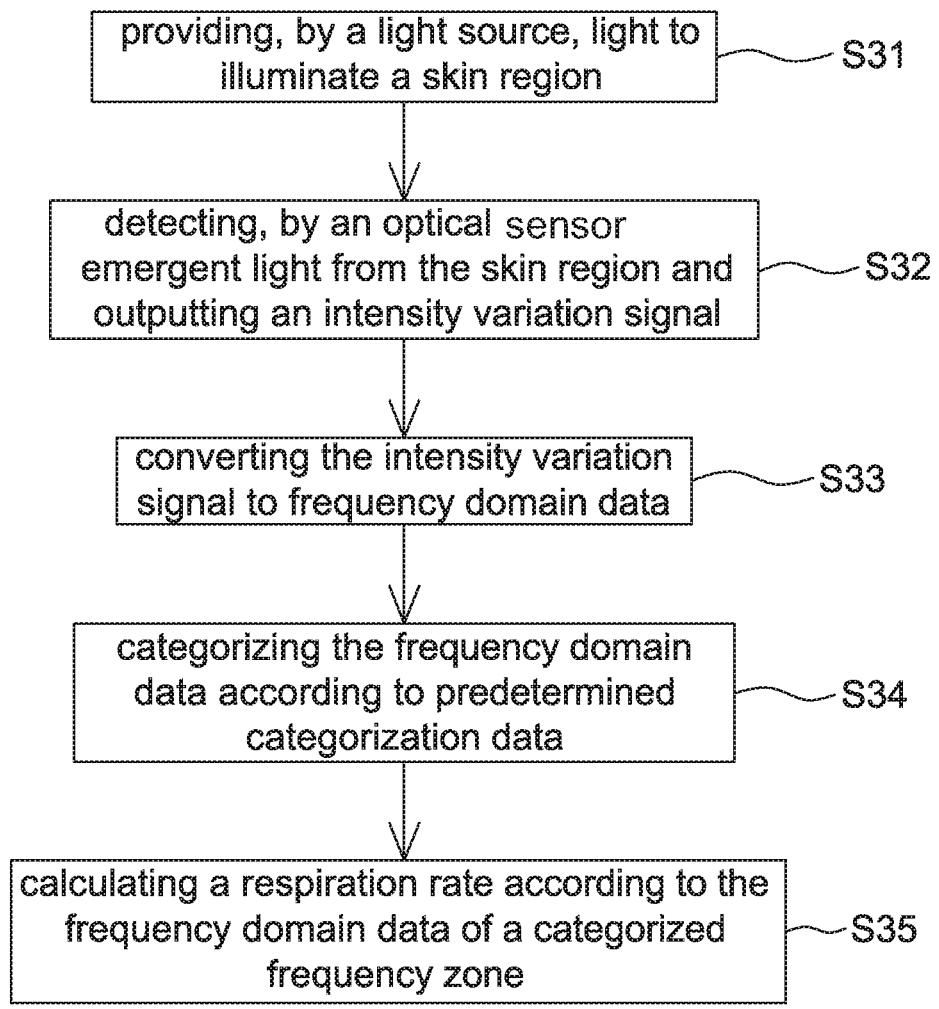
FIG. 11 is a flow chart of a respiration rate detection method according to one embodiment of the present disclosure.

Referring to FIG. 11, it is a flow chart of a respiration rate detection method according to one embodiment of the present disclosure including the steps of: providing, by a light source, light to illuminate a skin region (Step S31); detecting, by an optical sensor, emergent light from the skin region and outputting an intensity variation signal (Step S32); converting the intensity variation signal to frequency domain data (Step S33); categorizing the frequency domain data according to predetermined categorization data (Step S34); and calculating a respiration rate according to the frequency domain data of a categorized frequency zone (Step S35). The respiration rate detection method of this embodiment is applicable, for example, to the respiration rate detection device 900 of FIG. 9, and since details of implementation have been illustrated above, details thereof are not repeated herein.

As mentioned above, if the intensity variation signal is denoised by an acceleration signal at first, the frequency domain data is replaced by denoised first frequency domain information.

By using the respiration rate detection device and the respiration rate detection method of the embodiment of the present disclosure, the interference from noises outside the categorized frequency zone is removed thereby improving the detection accuracy.

Figure 12:
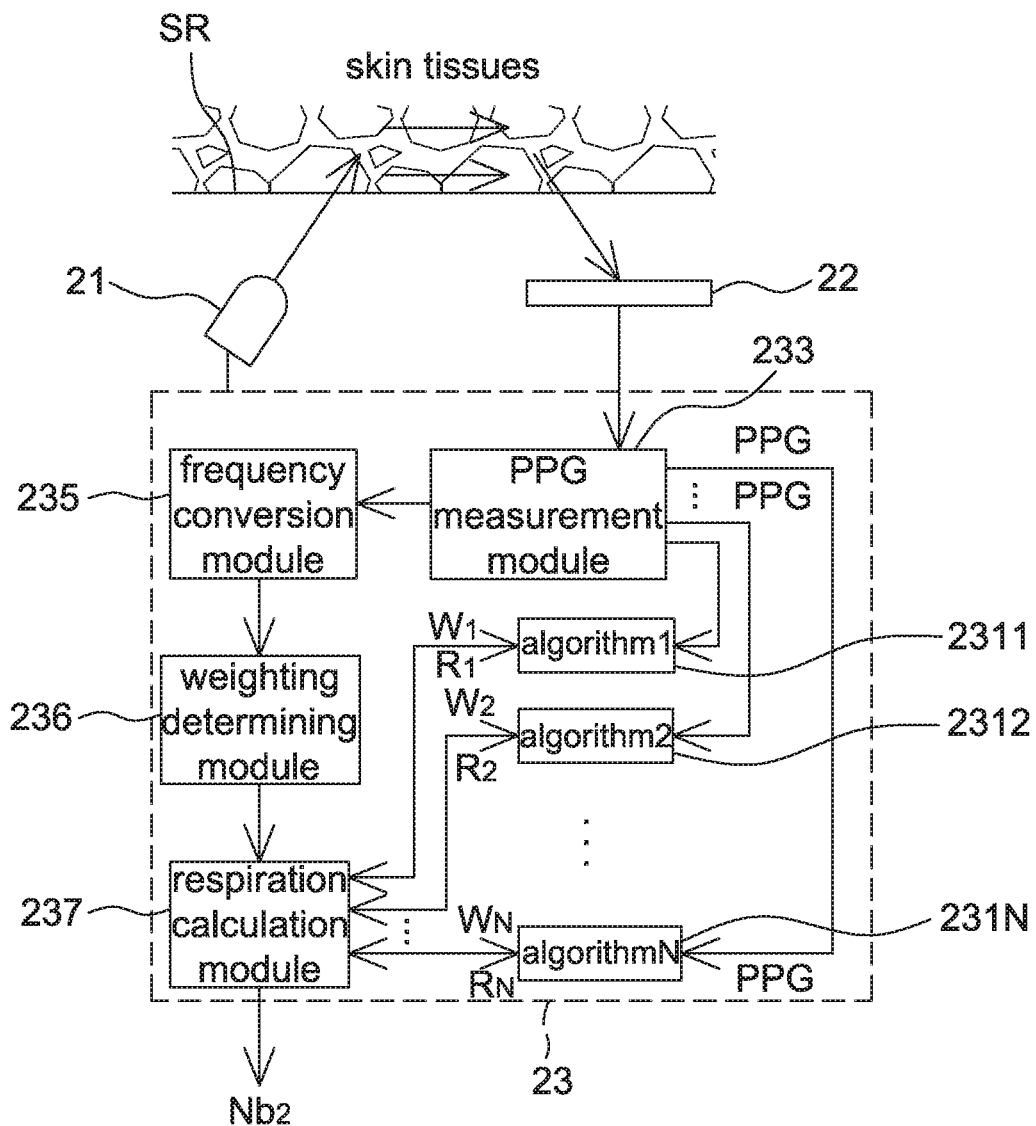
FIG. 12 is a schematic block diagram of a respiration rate detection device according to another embodiment of the present disclosure.

Referring to FIG. 12, it is a schematic block diagram of a respiration rate detection device 200 according to another embodiment of the present disclosure. The respiration rate detection device 200 determines a set of weightings and a set of respiration rate calculation algorithms according to a main frequency amplitude of a current PPG signal, takes respiration rates obtained by different respiration rate calculation algorithms as respiration rate components, and combines the respiration rate components according to the set of weightings to form an output respiration rate thereby improving the detection accuracy. The respiration rate detection device 200 includes a light source 21, an optical sensor 22 and a processor 23, wherein the light source 21 and the optical sensor 22 are similar to those of the above embodiment and thus details thereof are not repeated herein.

In this embodiment, the processor 23 is also selected from a digital signal processor (DSP), a microcontroller (MCU) or a central processor (CPU), and used to receive an intensity variation signal outputted from the optical sensor 22 and the acceleration signal outputted from a motion sensor 12 and perform the post-processing. The processor 23 converts the intensity variation signal into frequency domain data, determines a set of weightings and a set of respiration rate calculation algorithms according to a signal to noise ratio (SNR) of the frequency domain data, and calculates a respiration rate according to the set of weightings and the set of respiration rate calculation algorithms.

To denoise the PPG signal at first, the processor 23 respectively converts the PPG signal and the acceleration signal to first frequency domain information, which comprises a first frequency index set and a first spectrum value set associated with the first frequency index set, and second frequency domain information, which comprises a second frequency index set and a second spectrum value set associated with the second frequency index set. Then, the processor 23 identifies a plurality of frequency indexes corresponding to a plurality of spectrum peak values in the first frequency domain information and the second frequency domain information. The processor 23 further determines a reference index as a denoising parameter according to a frequency index corresponding to a maximum spectrum peak value of the second frequency domain information to denoise the first frequency domain information by removing spectrum values, which correspond to frequency indexes of the denoising parameter, from the first frequency domain information to generate denoised first frequency domain information. Details of these operations performed by the processor 23 have been described above, e.g., referring to FIGS. 4A-4B, 5A-5B, 6 and the corresponding descriptions thereof.

The processor 23 includes a PPG measurement module 233, a frequency conversion module 235, a weighting determining module 236, a respiration calculation module 237 and a plurality of respiration rate calculation units 2311 to 231N, wherein the function of the PPG measurement module 233 is similar to the PPG measurement module 933 of the above embodiment and thus details thereof are not repeated herein. For example, the light source 21, the optical sensor 22 and the PPG measurement module 233 in FIG. 12 form the PPG measuring device 10 in FIG. 1. The processor 23 includes the frequency conversion module 235, the weighting determining module 236, the respiration calculation module 237 and the respiration rate calculation units 2311 to 231N.

The frequency conversion module 235 converts the PPG signal (e.g., shown in FIG. 10A) outputted by the PPG measurement module 233 into frequency domain data (e.g., shown in FIG. 10B). It should be mentioned that although FIG. 12 shows functions performed by the processor 23 as different functional blocks, it is only intended to illustrate but not to limit the present disclosure. The functions performed by the PPG measurement module 233, the frequency conversion module 235, the weighting determining module 236, the respiration calculation module 237 and the plurality of respiration rate calculation units 2311 to 231N are all considered to be executed by the processor 23 and implemented by software, hardware or a combination thereof without particular limitations.

To denoise the PPG signal, the frequency conversion module 235 respectively converts the PPG signal from the PPG measurement module 233 and the acceleration signal from the motion sensor 12 to the first frequency domain information and the second frequency domain information as shown in FIGS. 4A-4B, 5A-5B and 6. Or the processor 23 has two conversion modules (as shown in FIG. 1) respectively converts the PPG signal to the first frequency domain information and converts the acceleration signal to the second frequency domain information. Details thereof have been described above, and thus are not repeated herein.

In the present disclosure, respiration rate calculation algorithms include, for example, directly performing the Fourier spectrum analysis on the PPG signal, acquiring respiration characteristics in the PPG signal (e.g. characteristics of amplitude variation or frequency variation) and then performing the Fourier spectrum analysis on the respiration characteristics, the independent component analysis and the adaptive noise filtering, without particular limitations. The respiration rate calculation algorithms also include the self-designed respiration rate calculation algorithm which calculates a current respiration rate in time domain or frequency domain. Any respiration rate calculation algorithms are applicable to the respiration rate detection device 200 as long as different respiration rate calculation algorithms correspond to different signal features, e.g., the signal to noise ratio or energy distribution, wherein said different signal features are used to determine the weighting corresponding to the associated respiration rate calculation algorithm. For example, although a distortion is not obvious by directly performing the Fourier spectrum analysis on the PPG signal, the result is easily influenced by ultra low frequency noises. Accordingly, when the respiration rate component obtained by the Fourier spectrum analysis is within an ultra low frequency zone, the weighting corresponding to the Fourier spectrum analysis is reduced so as to reduce the interference from noises within the ultra low frequency zone.

In one embodiment, it is assumed that the above four respiration rate calculation algorithms are used, and the weighting corresponding to each respiration rate calculation algorithm is assumed to be 1 at first. If a signal to noise ratio of the obtained frequency domain data (or denoised first frequency domain information if denoising by the acceleration signal is performed) is lower than a first threshold (e.g., threshold1), it means that the noise is obvious such that the weighting corresponding to the adaptive noise filtering is increased (e.g., increasing the weighting by 1). If the signal to noise ratio of the obtained frequency domain data (or the denoised first frequency domain information) is higher than a second threshold (e.g., threshold2), it means that the noise is not obvious such that the weighting corresponding to directly performing the Fourier spectrum analysis on the PPG signal is increased (e.g., increasing the weighting by 1). If a sum of spectral amplitudes of ultra low frequency signals (or a ratio of the sum of spectral amplitudes of ultra low frequency signals with respect to a sum of spectral amplitudes of low frequency signals) is higher than a third threshold (e.g., threshold3), it means that the respiration characteristics in the PPG signal are easily interfered by ultra low frequency noises such that the weighting corresponding to acquiring respiration characteristics in the PPG signal and then performing the Fourier spectrum analysis on the respiration characteristics is decreased (e.g., decreasing the weighting by 1) and/or the weighting corresponding to the independent component analysis is increased (e.g., increasing the weighting by 1). If a sum of spectral amplitudes of ultra low frequency signals (or a ratio of the sum of spectral amplitudes of ultra low frequency signals with respect to a sum of spectral amplitudes of low frequency signals) is lower than a fourth threshold (e.g., threshold4), the weighting corresponding to acquiring respiration characteristics in the PPG signal and then performing the Fourier spectrum analysis on the respiration characteristics is increased (e.g., increasing the weighting by 1).

Figures 13, 14:
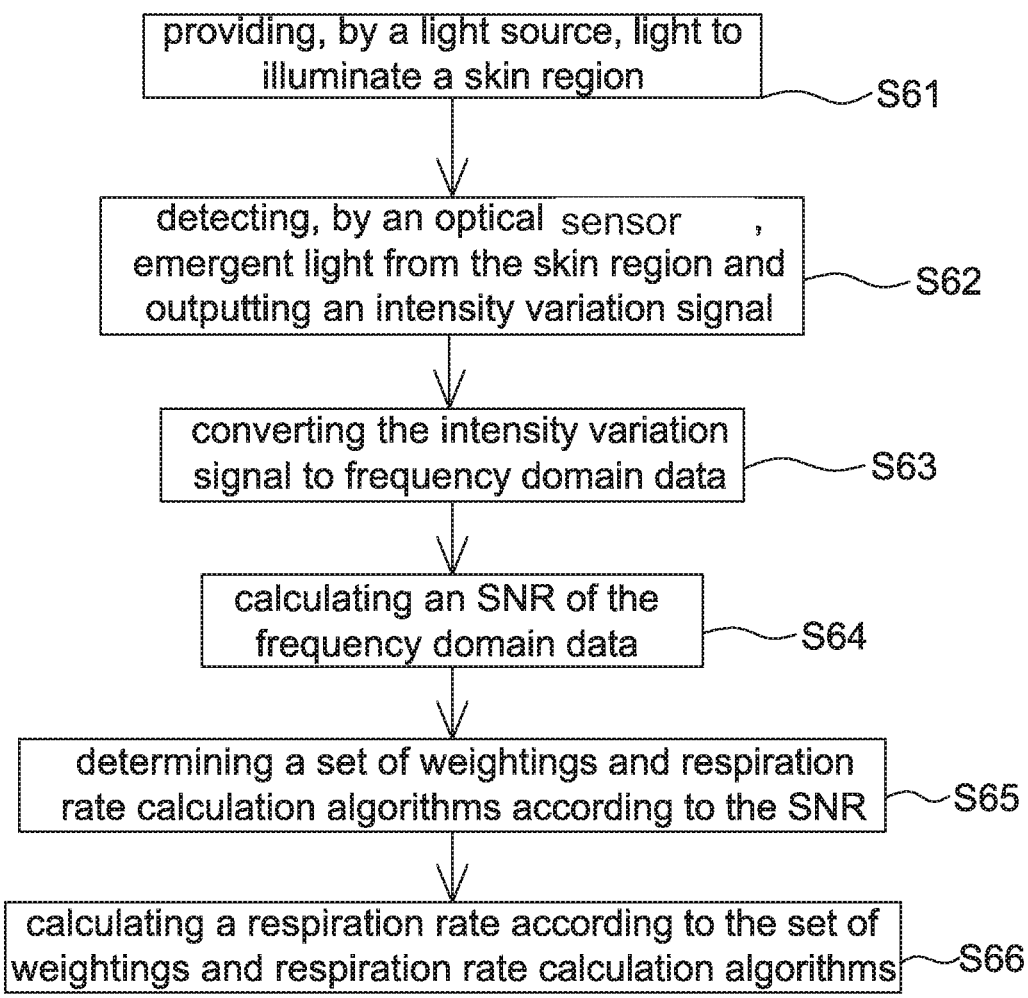
FIG. 13 is a schematic diagram of a look-up table of a respiration rate detection device according to another embodiment of the present disclosure.
FIG. 14 is a flow chart of a respiration rate detection method according to another embodiment of the present disclosure.

Next, referring to FIGS. 10B, 12-13, FIG. 13 is a schematic diagram of a look-up table of a respiration rate detection device according another embodiment of the present disclosure.

The weighting determining module 236 determines a set of weightings and a set of respiration rate calculation algorithms according to a signal to noise ratio (SNR) of the frequency domain data (or the denoised first frequency domain information). In some embodiments, the signal to noise ratio is a ratio of a maximum spectral amplitude with respect to a sum of other spectral amplitudes in the frequency domain data (or the denoised first frequency domain information). For example in FIG. 10B, the signal to noise ratio is a ratio of a spectral amplitude at Nb1' with respect to a sum of other spectral amplitudes. Accordingly, after the weighting determining module 236 obtains a signal to noise ratio, the signal to noise ratio is compared with a look-up table as shown in FIG. 13, wherein the relationship of a plurality of signal to noise ratios with respect to a plurality of weightings is previously built up to form the look-up table. In other words, the processor 23 is built in a plurality of respiration rate calculation algorithms (e.g., 2311 to 231N), and the selected set of respiration rate calculation algorithms includes at least one of the stored respiration rate calculation algorithms, and each signal to noise ratio (e.g., $SNR_1$ to $SNR_N$) corresponds to a set of weightings and an associated set of respiration rate calculation algorithms. It should be mentioned that although FIG. 13 shows the relationship of a plurality of signal to noise ratios with respect to a plurality of weightings, it is only intended to illustrate but not to limit the present disclosure. In some embodiments, the look-up table stores the relationship of a plurality of signal to noise ratio ranges with respect to a plurality of weightings. In other embodiments, the look-up table stores the relationship of a plurality of signal to noise ratios (or signal to noise ratio ranges) and frequency zones with respect to a plurality of weightings. In the present disclosure, the weighting may be between 0 and 1. In other words, when the weighting corresponding to one respiration rate calculation algorithm is 0, it means that the respiration rate calculation algorithm is not used. In other embodiments, the look-up table stores the relationship of a plurality of energy distributions (e.g., a sum of spectral amplitudes of ultra low frequency signals, a ratio of a sum of spectral amplitudes of ultra low frequency signals with respect to a sum of spectral amplitudes of low frequency signals) with respect to a plurality of weightings.

Finally, the respiration calculation module 237 calculates a respiration rate Nb2 according to the selected set of weightings and the selected set of respiration rate calculation algorithms. In one embodiment, each algorithm of the selected set of respiration rate calculation algorithms respectively calculates a respiration rate component $R_1, R_2 \ldots R_N$ according to the intensity variation signal. For example, the respiration rate Nb2 is a sum of products of each of the selected set of weightings $W_1, W_2 \ldots W_N$ and each of the respiration rate component $R_1, R_2 \ldots R_N$ obtained by the associated respiration rate calculation algorithm, i.e. $Nb2 = R_1 \times W_1 + R_2 \times W_2 + \ldots + R_N \times W_N$, wherein at least one of $R_1, R_2 \ldots R_N$ is not zero. In other words, according to actually acquired frequency domain data, it is possible that the respiration calculation module 237 calculates a current respiration rate according to one respiration rate calculation algorithm, and in this case the weighting corresponding to the one respiration rate calculation algorithm is set to 1 and the weightings corresponding to other respiration rate calculation algorithms are set to zero. That is, the above respiration rate components are the respiration rates obtained by every respiration rate calculation algorithm, and when a set of respiration rate calculation algorithms includes more than one respiration rate calculation algorithms, the respiration rate obtained by each of the more than one respiration rate calculation algorithms is not directly used as an output respiration rate and referred as a respiration rate component herein. When a set of respiration rate calculation algorithms includes one respiration rate calculation algorithm, the respiration rate component obtained by the one respiration rate calculation algorithm is used as an output respiration rate.

Referring to FIG. 14, it is a flow chart of a respiration rate detection method according to another embodiment of the present disclosure including the steps of: providing, by a light source, light to illuminate a skin region (Step S61); detecting, by an optical sensor, emergent light from the skin region and outputting an intensity variation signal (Step S62); converting the intensity variation signal to frequency domain data (Step S63); calculating a signal to noise ratio of the frequency domain data (Step S64); determining a set of weightings and a set of respiration rate calculation algorithms according to the signal to noise ratio (Step S65); and calculating a respiration rate according to the set of weightings and the set of respiration rate calculation algorithms (Step S66). The respiration rate detection method of this embodiment is applicable to the respiration rate detection device 200 of FIG. 12.

As mentioned above, if the intensity variation signal is denoised by an acceleration signal at first, the frequency domain data is replaced by denoised first frequency domain information as mentioned above.

Referring to FIGS. 10A-10B and 12-14, details of this embodiment are illustrated hereinafter.

Step S61: The light source 21 emits light of a predetermined optical spectrum to illuminate a skin region SR. As described in the above embodiment, corresponding to different applications, it is possible that the respiration rate detection device 200 includes more than one light source.

Step S62: The optical sensor 22 detects emergent light from the skin region SR and outputs an intensity variation signal. As described in the above embodiment, the optical sensor 22 is a light emitting diode or an image sensor having a pixel array.

Step S63: As described in the above embodiment, the PPG measurement module 233 continuously acquires the intensity variation signal within a time interval (e.g., 5 to 10 seconds) to be used as the PPG signal, wherein according to different embodiments of the optical sensor 22, the intensity variation signal is the intensity signals or a sum of intensity signals within a time interval. The frequency conversion module 235 converts the intensity variation signal (or the PPG signal) into frequency domain data.

If the PPG signal is denoised by an acceleration signal, the processor 23 further receives and convers the acceleration signal into frequency domain information as shown FIGS. 5A-5B and 6.

Step S64: The weighting determining unit 236 calculates a signal to noise ratio of the frequency domain data (or the denoised first frequency domain information) at first. For example, the weighting determining unit 236 determines a main frequency, e.g., Nb1' shown in FIG. 10B having a maximum spectral amplitude and taken as the main frequency, in the frequency domain data (or the denoised first frequency domain information) at first. Then, the weighting determining unit 236 calculates a ratio of a spectral amplitude of the main frequency with respect to a sum of other spectral amplitudes in the frequency domain data (or the denoised first frequency domain information) to be used as the signal to noise ratio herein.

Step S65: Then, the weighting determining unit 236 compares the signal to noise ratio with a look-up table (as shown in FIG. 13) to determine a set of weightings and a set of respiration rate calculation algorithms. As mentioned above, the look-up table previously stores the relationship of a plurality of signal to noise ratios (or a plurality of signal to noise ranges) with respect to a plurality of weightings, e.g., storing in a memory of the processor 23. Accordingly, when the weighting determining unit 236 obtains a signal to noise ratio, a set of weightings and a set of respiration rate calculation algorithms are determined correspondingly.

After the set of respiration rate calculation algorithms is determined, each algorithm of the determined set of respiration rate calculation algorithms respectively calculates a respiration rate component $R_1, R_2 \ldots R_N$ according to the intensity variation signal (or the PPG signal). It is appreciated that the respiration rate calculation algorithm not included in the selected set of respiration rate calculation algorithms does not operate so as to reduce the system resources.

Step S66: Finally, the respiration calculation module 237 calculates a sum of products of each of the set of weightings $W_1, W_2 \ldots W_N$ and each of the respiration rate components $R_1, R_2 \ldots R_N$ obtained by the set of respiration rate calculation algorithms corresponding to the set of weightings, e.g., $Nb2 = R_1 \times W_1 + R_2 \times W_2 + \ldots + R_N \times W_N$, and the sum of products Nb2 is then outputted.

In the present disclosure, the respiration rate Nb1 or Nb2 outputted by the processor 93 or 23 is applicable to different applications, e.g., being displayed, being compared with at least one threshold, being recorded and so on without particular limitations.

In some embodiments, the respiration rate detection methods in the above embodiments are combinable to further improve the detection accuracy. For example, one embodiment is initially used to remove the frequency domain data in some frequency zones, and then another embodiment is used to calculate the frequency domain data being left (e.g., the frequency domain data in the ultra low frequency zone or in the low frequency zone shown in FIG. 10B). Details of the two embodiments are illustrated above, and thus are not repeated herein.

It should be mentioned that although FIGS. 9 and 12 show that the light sources 91 and 21 and the optical sensors 92 and 22 are located at a same side of a skin region SR to form a reflective detection device, it is only intended to illustrate but not to limit the present disclosure. In other embodiments, the light source and the optical sensor are located at opposite sides of the skin region to form a transmissive detection device.

In one embodiment, the intensity variation signal (or PPG signal) is firstly denoised using an acceleration signal that is detected by a motion sensor within a detection period for detecting the PPG signal. After obtaining denoised frequency domain information, the processor 93 and 23 in FIGS. 9 and 12 calculates a respiration rate by replacing the above frequency domain data by the denoised frequency domain information, and other operations are not changed.

In another embodiment, after the denoised first frequency domain information is obtained as mentioned above, the processor further determines a breathing signal according to the denoised first frequency domain information. To determine the breathing signal in time domain, the processor converts the denoised first frequency domain information to time domain to generate a denoised PPG signal, and acquire a low frequency carrier of the denoised PPG signal as the breathing signal. To determine the breathing signal in frequency domain, the processor determines the breathing signal as a spectrum range in the first frequency domain information lower than 0.25 Hz.

More specifically, the breathing signal, which may be shown on a display device, in this embodiment is referred to a spectrum signal in frequency domain or a time-varying signal in time domain.

Photoplethysmography (PPG) signals are consisted of two parts. When a systole occurs, the blood pressure and blood volume in blood vessels of the whole body have a continuous variation. When a diastole occurs, the blood pressure decreases correspondingly and the blood pumped-out in a previous systole heats the heart valve to cause so-called inflection.

Therefore, a complete PPG waveform includes a mixed effect of said systole and pressures from the blood vessel wall. The PPG signal is obtainable by detecting a volume variation of blood vessels through optical measurements.

To obtain signals related to a user's breathing signal from a PPG signal, it is necessary to obtain the PPG signal at first, and a low frequency carrier of the PPG signal is then identified to determine a corresponding frequency of the low frequency carrier, wherein the frequency of the low frequency carrier is used to represent a breathing cycle period of the user.

The low frequency carrier includes rising parts and falling parts, wherein the rising parts are used to represent one of the breathe-out and the breathe-in of a user, and the falling parts are used to represent the other one of the breathe-out and the breathe-in of the user. Meanwhile, it is able to real-timely provide at least one of the breathing cycle period, the breathe-out and the breathe-in to the user for reference or suggesting the user to adjust the breathing pattern and/or the breathing depth.

As mentioned above, a complete PPG waveform includes a mixed effect of the systole and pressures from blood vessels. In the present disclosure, a volume variation of blood vessels is detected by optical measurements to obtain said PPG signals.

As mentioned above, it is possible to use a PPG signal to indicate a frequency of the heart circulation. As the PPG signal is to detect a volume variation of blood vessels and all blood vessels in the human body are connected together, related information of a breathing depth and a breathing cycle period are obtainable from analyzed signals through analyzing the PPG signal.

For example, when a breathe-in occurs, muscular exertion squeezes blood vessels and causes the value of a PPG signal to rise up; on the contrary, when a breathe-out occurs, muscle relaxation causes the value of a PPG signal to fall down. A breathing frequency of the breathing system of a user is identifiable by analyzing the rising period and/or the falling period of the PPG signal.

In addition, by comparing with the user's activity, it is possible to arrange a breath detection system to output a prompt to direct a user how to adjust breaths. To be more precisely, it is able to suggest the user to adjust a breathing frequency, and a depth and speed of breathe-in and/or breathe-out. For example, when a user has the hyperventilation due to nervousness, it is able to suggest the user to relax from an equipment which is connected to the detected PPG signal; or when a user breathes too fast or too slow during exercising, it is able to suggest the user to adjust the breath pattern to match the current exercise strength. It is able to suggest the user by an auditory prompt such as a voice or music through a user's earphone, by a visual prompt through a user's portable device, or by body sensing, e.g., the vibration.

One embodiment of obtaining the breathe-in, the breathe-out and the breathing cycle period related to the user's breathing from a PPG signal is illustrated hereinafter.

Figure 15:
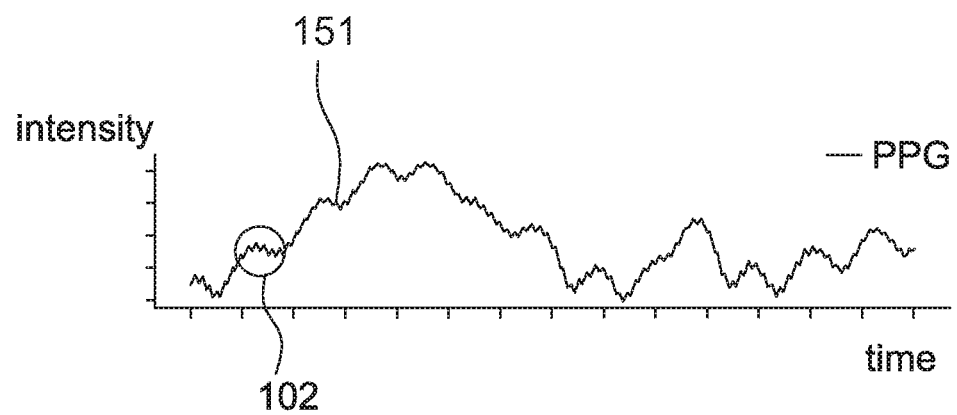
FIG. 15 is a photoplethysmography (PPG) signal.
Figure 16:
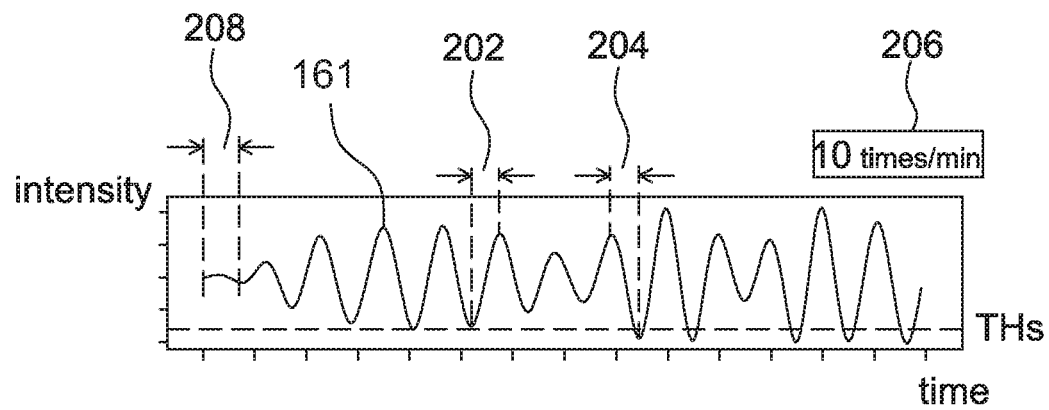
FIG. 16 is a schematic diagram of breathing cycle periods of the PPG signal retrieved from FIG. 1, each period including a rising part and a falling part.

Firstly, a PPG signal 151 is obtained by a breath detection device. As shown in FIG. 15, a high frequency part 102 of the PPG signal 151 indicates a frequency of the heart circulation. A low frequency carrier of the PPG signal 151 is then identified to determine one corresponding low frequency carrier signal 161, which has a low frequency capable of being used to indicate a breathing cycle period of a user, as shown in FIG. 16. Compared with FIG. 15, it is seen that there is a relationship between a variation speed of the low frequency carrier signal 161 in FIG. 16 and a carrier of the PPG signal 151 in FIG. 15.

To denoise motion noises from the PPG signal 151, an acceleration signal is detected (as shown in FIG. 1) and used to denoise the PPG signal 151 at first to generate denoised frequency domain information. In one aspect, the denoised frequency domain information is directly used to determine a breathing signal in frequency domain. In another aspect, the denoised frequency domain information is converted to time domain to generate a denoised PPG signal at first. The denoised PPG signal is then used to generate the low frequency carrier signal 161.

In one embodiment of the present disclosure, the breath detection device is further able to identify a rising part 202 and a falling part 204 of the low frequency carrier signal 161. As shown in one embodiment of FIG. 16, the rising part 202 represents a breathe-in and the falling part 204 represents a breathe-out. In other embodiments, due to the different processing of the obtained signal, it is possible that the rising part 202 represents a breathe-out and the falling part 204 represents a breathe-in. After obtaining the above information, it is able to real-timely output at least one of the breathing cycle period, the breathe-in and the breathe-out, and to suggest a user to adjust the whole breathing frequency or at least one of the breathe-in and the breathe-out. It is seen from FIG. 16 that high points and low points of the PPG signal in FIG. 15 do not exactly correspond to peaks and valleys of the low frequency carrier signal 161 in FIG. 16.

To be more precisely, FIG. 16 shows that each breath of a user is not exactly the same. Perhaps the frequency of breaths may be maintained almost the same, but the depth (e.g., amplitude) of the breathe-out and the breathe-in still changes. A user is hardly conscious of this change by him/herself in daily life. Therefore, by using the breath detection device in the embodiment of the present disclosure, it is able to help the user to understand his/her physiological states more, and achieve the effect of self-adjustment.

The present disclosure is also able to record user's breathing states for a long period of time to provide statistical data to the user as a reference for the self-adjustment, and it is possible to further determine thresholds according to said statistical data.

Figures 17A, 17B:
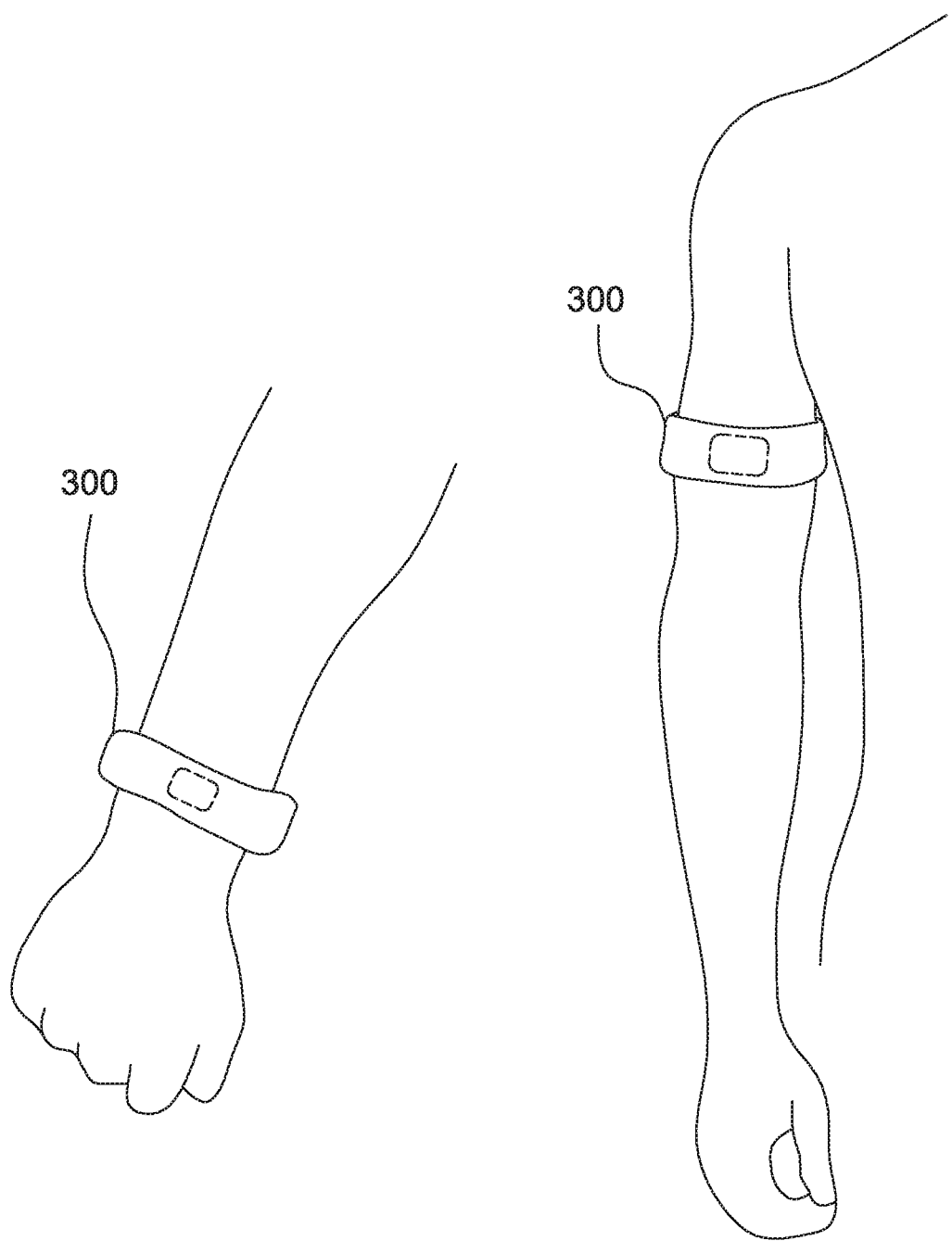
FIGS. 17A and 17B are usage states of a breath detection device according to some embodiments of the present disclosure.

Please referring to FIGS. 17A and 17B, they are usage states of a breath detection device according to some embodiments of the present disclosure. The breath detection device 300 analyzes and displays the variation of a user's breathing signal changed with time, as shown in FIG. 16, by detecting a PPG signal of the user's skin tissues. Accordingly, the breath detection device 300 is able to be arranged at any suitable location to detect the PPG signal, e.g., setting on the user's wrist (FIG. 17A) or the user's arm (FIG. 17B), but not limited thereto. In another embodiment, the breath detection device 300 is integrated in a portable electronic device or a wearable electronic device, e.g., a bracelet, an armband, a ring, a foot ring, a foot bracelet, a cell phone, an earphone, a headphone and a personal digital assistant (PDA) which contacts at least a part of skin surface of a user. In addition, the breath detection device 300 is able to be coupled to a medical device, a home appliance, a vehicle, a security system in a wired or wireless way. Preferably, the one connected with the breath detection device 300 includes a display device to real-timely display a detection result of the breath detection device 300, e.g., directly displaying the low frequency carrier signal 161 as shown in FIG. 16.

Figure 18:
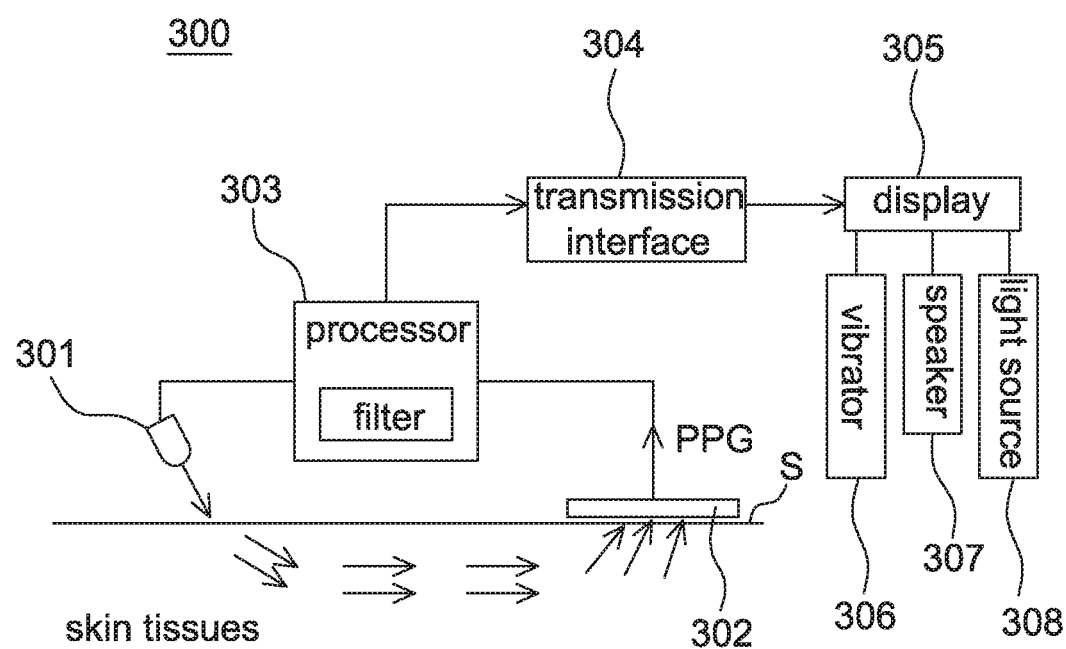
FIG. 18 is a schematic block diagram of a breath detection device according to one embodiment of the present disclosure.
Figure 19:
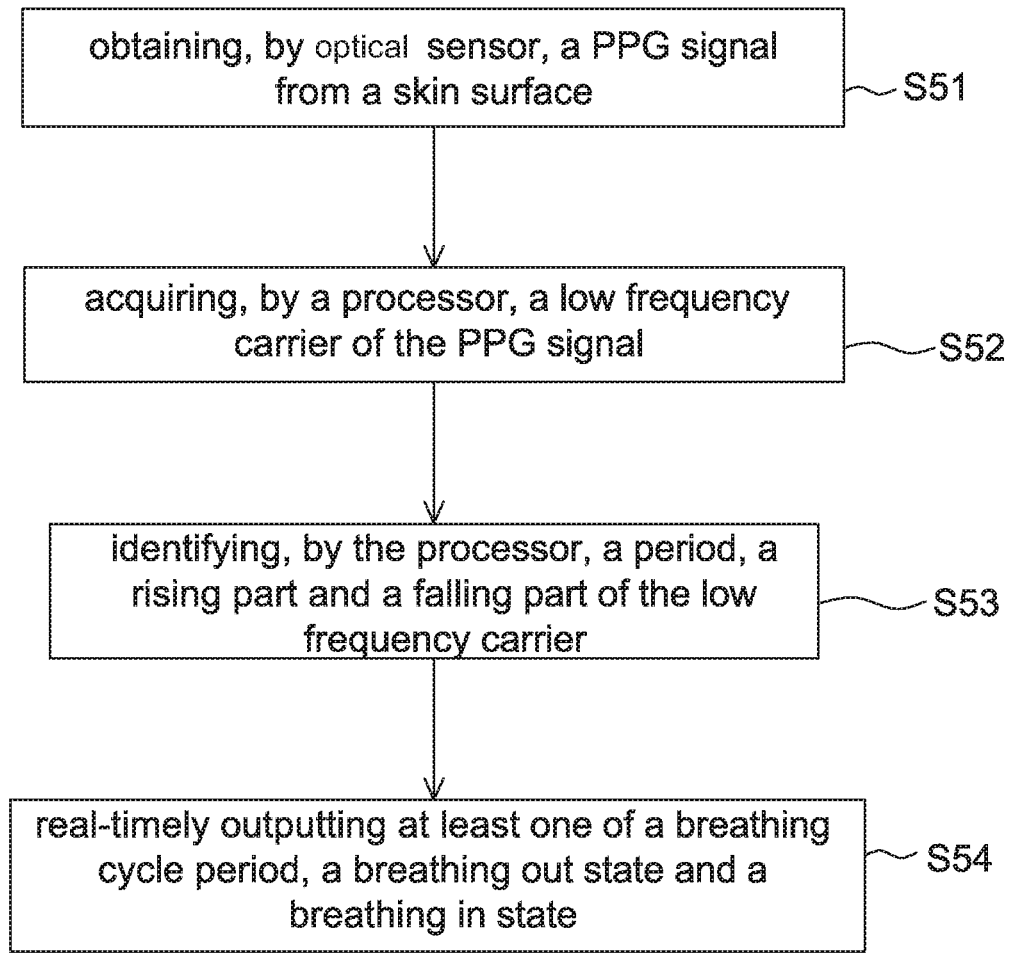
FIG. 19 is a flow chart of an operating method of a breath detection device according to one embodiment of the present disclosure.

Please referring to FIG. 18, it is a schematic block diagram of a breath detection device 300 according to one embodiment of the present disclosure. The breath detection device 300 includes a light source 301, an optical sensor 302 and a processor 303. In some embodiments, the breath detection device 300 further includes a display device 305 configured to display the detection result of the breath detection device 300. In some embodiments, the breath detection device 300 further includes a transmission interface 304 coupled to an external display device 305 in a wired or wireless manner to output the detection result (e.g., low frequency carrier signal 161 or breathing spectrum signal) of the breath detection device 300 to the display device 305 to be real-timely displayed. In other words, the display device 305 may or may not be included in the breath detection device 300 depending on different applications. The display device 305 is, for example, a liquid-crystal display (LCD), a plasma display panel (PDP), an organic light-emitting diode (OLED) display or a projector for displaying images without particular limitations as long as it is able to display the low frequency carrier signal 161 as shown in FIG. 16 or a breathing spectrum signal on a screen thereof.

In the embodiment to denoise the PPG signal at first, the breath detection device 300 further includes a motion sensor (e.g., 12 shown in FIG. 1) to output a motion signal to the processor 303. The processor 303 respectively converts the PPG signal and the acceleration signal to first frequency domain information, which comprises a first frequency index set and a first spectrum value set associated with the first frequency index set (e.g., referring to FIGS. 4A-4B), and second frequency domain information, which comprises a second frequency index set and a second spectrum value set associated with the second frequency index set (e.g., referring to FIGS. 5A-5B), identifies a plurality of frequency indexes corresponding to a plurality of spectrum peak values in the first frequency domain information and the second frequency domain information, determines a reference index as a denoising parameter according to a frequency index corresponding to a maximum spectrum peak value of the second frequency domain information to denoise the first frequency domain information by removing spectrum values, which correspond to frequency indexes of the denoising parameter, from the first frequency domain information to generate denoised first frequency domain information (e.g., referring to FIG. 6), and determines a breathing signal according to the denoised first frequency domain information. Details of obtaining the denoised first frequency domain information have been illustrated above, and thus are not repeated herein.

To obtain time-varying breathing signal, the processor 303 further converts the denoised first frequency domain information to time domain to generate a denoised PPG signal. The conversion from the denoised first frequency domain information to the denoised PPG signal is performed by inverse DFT or inverse FFT. The processor 303 then acquires a low frequency carrier of the denoised PPG signal as the breathing signal. To obtain breathing spectrum signal, the processor 303 directly determines the breathing signal as a spectrum range in the first frequency domain information lower than 0.25 Hz. For example, a peak value in the breathing spectrum signal indicates a breathing frequency.

The light source 301 is, for example, a light emitting diode or a laser diode, configured to emit light adapted to penetrate and be absorbed by skin tissues. For example, a wavelength of light emitted by the light source is about 610 nm or 910 nm, but not limited thereto. The light source 301 illuminates a skin surface S to allow light to pass through skin tissues under the skin surface S. Preferably, the breath detection device 300 includes a transparent surface to be attached to the skin surface S in operation and for protecting the light source 301, and the light source 301 is arranged at an inner side of the transparent surface. The transparent surface is made of, e.g., plastic or glass without particular limitations.

In some embodiments, when the breath detection device 300 also detects the blood oxygenation, the breath detection device 300 includes two light sources to respectively emit different wavelengths of light, wherein the method of detecting the blood oxygenation may be referred to U.S. application Ser. No. 13/614,999 assigned to the same assignee of the present application, and the full disclosure of which is incorporated herein by reference.

The optical sensor 302 is, for example, a photodiode or an image sensor array, e.g., a CMOS sensor array, and configured to detect ejected light emitted from the skin tissues to generate a PPG signal, as shown in FIG. 15 for example. The method of detecting and outputting a PPG signal by a photodiode is known to the art and thus details thereof are not described herein. The present disclosure is to identify breathing signals according to the detected PPG signal (or denoised PPG signal if denoising by the acceleration signal is performed). The method of detecting a three dimensional physiology distribution by an image sensor array may be referred to U.S. application Ser. No. 14/955,463 assigned to the same assignee of the present application, and the full disclosure of which is incorporated here by reference. Similarly, the optical sensor 302 is arranged inside of the transparent surface.

The processor 303 is, for example, a microcontroller (MCU), a central processing unit (CPU) or an application specific integrated circuit (ASIC), which is electrically coupled to the light source 301 and the optical sensor 302, and configured to control the light source 301 and the optical sensor 302 to operate correspondingly. The processor 303 acquires a low frequency carrier (e.g., the low frequency carrier signal 161 shown in FIG. 16) of the PPG signal (as shown in FIG. 15 for example) or the denoised PPG signal as a breathing signal, wherein said acquiring is implemented by software and/or hardware without particular limitations. For example, the processor 303 acquires the low frequency carrier signal 161 from the PPG signal or the denoised PPG signal by a digital band pass filter. Generally, a user's respiration rate is lower than 15 times per minute, so a pass band of the digital band pass filter is preferably lower than 0.25 Hz. It is appreciated that the pass band of the digital band pass filter is set according to the operation situation of the breath detection device 300 without particular limitations.

The transmission interface 304 outputs the breathing signal in a wired or wireless way, e.g., outputting data of the breathing signal at a predetermined frequency to a display device 305, wherein said wired and wireless transmission techniques are known to the art and thus details thereof are not described herein. It is appreciated that when the breath detection device 300 also includes the display device 305, the transmission interface 304 is not implemented or the transmission interface 304 is arranged inside the breath detection device 300 between the processor 303 and the display device 305.

The display device 305 real-timely displays a variation curve (i.e. the low frequency carrier signal 161) of the breathing signal changed with time as shown in FIG. 16 or displays a spectrum signal in frequency domain. In addition, the processor 303 further calculates an intensity threshold THs correlated to the breathing signal (as shown in FIG. 16), a rising part 202, a falling part 204 and a frequency value 206, and sends the values and data to the display device 305 directly or via the transmission interface 304 to be displayed thereon. For example, lines, numbers or graphics are shown on a screen of the display device 305 to mark the intensity threshold THs, the rising part 202, the falling part 204 and the frequency value 206 to allow a user to easily observe his/her breathing states from the display device 305.

Different from conventional breath detection devices, the breath detection device 300 of the present disclosure is able to real-timely display a user's breathing state. In other words, as the breath detection device 300 analyzes a PPG signal detected by the optical sensor 302 or the denoised PPG signal generated by the processor 303 to acquire a breathing signal, when the processor 303 receives the PPG signal, the processor 303 starts to analyze and output the breathing signal to the display device 305 to be displayed thereon. Accordingly, although an initial stage of the breathing signal displayed by the display device 305 includes a convergence time 208 (e.g., as shown in FIG. 16), a time interval of the convergence time 208 is determined by the digital filter being used. The breathing signal is displayed normally after the convergence time 208. Generally, the convergence time is not long and lower than several seconds.

In addition, to improve the user experience, the breath detection device 300 further includes a prompt device (e.g., display device 305) to output a prompt signal according to a comparison result of comparing detected values, e.g., an intensity, an average intensity, a rising part, a falling part and/or a frequency, of the variation curve with at least one threshold, wherein the prompt signal is, e.g., a vibration signal, a light signal, an audio signal and/or an image signal without particular limitations as long as the user can be informed.

The breath detection device 300 of the present disclosure is applicable to the breathing control.

For example, when a user's breathing depth does not reach or exceeds a threshold, the prompt device 305 outputs a prompt signal. In one embodiment of the present disclosure, the intensity (i.e. amplitude) or average intensity of the variation curve of the breathing signal is used to represent a user's breathing depth, i.e. the higher the intensity, the longer the user's breathing; on the contrary, the lower the intensity, the shorter the user's breathing.

For example, when a user's breathing time does not reach or exceeds a threshold, the prompt device 305 outputs a prompt signal. In one embodiment of the present disclosure, the rising part 202 of the variation curve of the breathing signal is used to represent one of a breathing in state and the breathing out state of a user, and the falling part 204 of the variation curve of the breathing signal is used to represent the other one of the breathing in state and the breathing out state of the user, i.e. the longer the rising part 202 and the falling part 204, the longer the user's breathing time; on the contrary, the shorter the rising part 202 and the falling part 204, the shorter the user's breathing time.

For example, when a user's breathing frequency does not reach or exceeds a threshold, the prompt device 305 outputs a prompt signal. In one embodiment of the present disclosure, the frequency is used to represent a respiration rate of a user, e.g., displayed by a frequency value 206 together with the breathing signal (i.e. the low frequency carrier signal 161 or breathing frequency signal) on a display screen. In this embodiment, the processor 303 is able to calculate the breathing frequency according to one rising part 202 and one falling part 204 (e.g., calculating a reciprocal of a sum of interval of the rising part 202 and the falling part 204) or directly according to a peak value in the breathing frequency signal, and it is not necessary to accumulate count values for one minute.

The indicating method of the prompt signal is determined according to different applications.

For example, the display device 305 may also be used as the prompt device. When the detected values exceed or do not reach the threshold, the processor 303 provides image signals to the display device 305 to make the display device 305 display the prompt, e.g., by words, graphs, and/or brightness, etc.

For example, the breath detection device 300 further includes a vibrator 306 used as the prompt device. When the detected values exceed or do not reach the threshold, the processor 303 provides vibration signals to the vibrator 306 to make the vibrator 306 generate vibrations to hint the user.

For example, the breath detection device 300 further includes a speaker 307 used as the prompt device. When the detected values exceed or do not reach the threshold, the processor 303 provides voice signals to the speaker 307 to make the speaker 307 generate sounds to hint the user.

For example, the breath detection device 300 further includes a warning light source 308 used as the prompt device. When the detected values exceed or do not reach the threshold, the processor 303 provides optical signals to the warning light source 308 make the warning light source 308 illuminate light to hint the user.

In some embodiments, the processor 303 includes, for example, a learning algorithm (e.g., implemented by software and/or hardware), and the above thresholds (e.g., intensity threshold, time threshold and frequency threshold, but not limited thereto) are determined according to the user's history records. Information related to the history records is stored in, for example, a non-volatile memory.

Please referring to FIG. 18, it is a flow chart of an operating method of a breath detection device according to one embodiment of the present disclosure, which includes the steps of: obtaining, by an optical sensor, a PPG signal from a skin surface (step S51); acquiring, by a processor, a low frequency carrier of the PPG signal (step S52); identifying, by the processor, a period, a rising part and a falling part of the low frequency carrier (step S53), and real-timely outputting at least one of a breathing cycle period, a breathing out state and a breathing in state (step S54).

Step S51: The breath detection device 300 is preferably fixed with respect to a skin surface S in operation such that a PPG signal detected by the optical sensor 302 is not affected by noises due to movement. In addition, the processor 303 further built-in with an algorithm for eliminating the noises in PPG signals caused by the movement, wherein the method of eliminating motion noises may be referred to U.S. application Ser. No. 13/614,999 assigned to the same assignee of the present application, and the full disclosure of which is incorporated herein by reference. The noise elimination is further performed using FIGS. 4A-4B, 5A-5B and 6 to generate denoised first frequency domain information. The processor 303 then obtains the breathing signal in time domain or frequency domain according to the denoised first frequency domain information.

Step S52: The processor 303 starts to acquire a low frequency carrier signal 161 (as shown in FIG. 16) from a PPG signal or the denoised PPG signal right after receiving the PPG signal from the optical sensor 302. In one embodiment, the processor 303 acquires the low frequency carrier signal 161 from the PPG signal or the denoised PPG signal using a digital band pass filter.

Step S53: After the processor 303 obtains the low frequency carrier signal 161, the processor 303 real-timely identifies a period, a rising part 202 and a falling part 204 of the low frequency carrier signal 161, wherein the period is used to indicate a user's breathing cycle period (e.g., including a rising part 202 and a falling part 204 adjacent to each other); the rising part 202 is used to indicate one of the user's breathe-in and breathe-out; and the falling part 204 is used to indicate the other one of the user's breathe-in and breathe-out. As mentioned above, in this embodiment the breath detection device 300 (or the processor 303) calculates a respiration rate of a user according to one breathing cycle period or directly using a peak value in the breathing spectrum signal (e.g., spectrum range in the denoised first frequency domain information smaller than 0.25 Hz).

Step S54: Next, the processor 303 outputs at least one of the breathing cycle period, a breathing out state of the breathe-out and a breathing in state of the breathe-in to the display device 305 to be real-timely displayed thereon. In one embodiment, the display device 305 displays a variation curve of the low frequency carrier signal 161 changed with time such that the breathing cycle period, the breathing out state and the breathing in state are displayed at the same time. In another embodiment, the display device 305 displays values of the breathing cycle period, the breathing out state and the breathing in state instead of displaying the variation curve. In another embodiment, the display device 305 displays both of a variation curve of the low frequency carrier signal 161 with time as well as values of the breathing cycle period, the breathing out state and the breathing in state. Furthermore, the display device 305 further shows at least one of an intensity threshold mark, a rising part mark, a falling part mark with lines, characters or graphs to help a user to easily read information.

As mentioned above, the conventional pulse oximeter of the heart rate detection module generates incorrect PPG signals when calculating a heart rate under a condition of a non-static state thereby decreasing the calculation accuracy of the heart rate. Therefore, the present disclosure further provides a heart rate detection module with a denoising function (e.g. FIG. 1), a detection method thereof (e.g. FIG. 2) and a denoising method thereof (e.g. FIG. 7) that may determine a denoising parameter through an acceleration signal to eliminate noise in a PPG signal so that the calculation accuracy of the heart rate is increased.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A respiration rate detection device, comprising:
an optical sensor configured to detect emergent light from a skin region in a detection period to output a PPG signal;
a motion sensor configured to output an acceleration signal corresponding to the detection period;
a band pass filter configured to filter the PPG signal and the acceleration signal; and
a processor configured to
respectively convert the filtered PPG signal and the filtered acceleration signal to first frequency domain information, which comprises a first frequency index set and a first spectrum value set associated with the first frequency index set, and second frequency domain information, which comprises a second frequency index set and a second spectrum value set associated with the second frequency index set,
identify a plurality of frequency indexes corresponding to a plurality of spectrum peak values in the first frequency domain information and the second frequency domain information,
determine a reference index as a denoising parameter according to a frequency index corresponding to a maximum spectrum peak value of the second frequency domain information to denoise the first frequency domain information by removing spectrum values, which correspond to frequency indexes of the denoising parameter, from the first frequency domain information to generate denoised first frequency domain information,
categorize the denoised first frequency domain information as one of a plurality of frequency zones according to predetermined categorization data, and
calculate a respiration rate according to the denoised first frequency domain information within the categorized frequency zone.

2. The respiration rate detection device as claimed in claim 1, wherein the predetermined categorization data is previously built up by a machine learning algorithm.

3. The respiration rate detection device as claimed in claim 1, wherein the processor is configured to distinguish two frequency zones with an isolation frequency, and the isolation frequency is between 0.15 Hz and 0.25 Hz.

4. The respiration rate detection device as claimed in claim 1, wherein the processor is configured to ignore the denoised first frequency domain information outside the categorized frequency zone.

5. The respiration rate detection device as claimed in claim 1, wherein the processor is configured to identify a frequency corresponding to a maximum spectral amplitude in the categorized frequency zone as the respiration rate.

6. The respiration rate detection device as claimed in claim 1, wherein
the optical sensor comprises a pixel array,
each pixel of the pixel array is configured to output an intensity signal within a frame, and
the processor is further configured to calculate a sum of the intensity signals of a plurality of pixels of the frame.

7. The respiration rate detection device as claimed in claim 1, wherein
the first frequency index set and the second index set have an identical number of frequency indexes.

8. The respiration rate detection device as claimed in claim 1, wherein
the processor is further configured to calculate a half of the reference index and a double of the reference index, and
the denoising parameter further comprises at least one of the half of the reference index and the double of the reference index.

9. A respiration rate detection device, comprising:
an optical sensor configured to detect emergent light from a skin region in a detection period to output a PPG signal;
a motion sensor configured to output an acceleration signal corresponding to the detection period;
a band pass filter configured to filter the PPG signal and the acceleration signal; and
a processor configured to
respectively convert the filtered PPG signal and the filtered acceleration signal to first frequency domain information, which comprises a first frequency index set and a first spectrum value set associated with the first frequency index set, and second frequency domain information, which comprises a second frequency index set and a second spectrum value set associated with the second frequency index set,
identify a plurality of frequency indexes corresponding to a plurality of spectrum peak values in the first frequency domain information and the second frequency domain information,
determine a reference index as a denoising parameter according to a frequency index corresponding to a maximum spectrum peak value of the second frequency domain information to denoise the first frequency domain information by removing spectrum values, which correspond to frequency indexes of the denoising parameter, from the first frequency domain information to generate denoised first frequency domain information,
determine a set of weightings and a set of respiration rate calculation algorithms according to a signal feature of the denoised first frequency domain information, and
calculate a respiration rate according to the set of weightings and the set of respiration rate calculation algorithms.

10. The respiration rate detection device as claimed in claim 9, wherein the signal feature is a signal to noise ratio, and the signal to noise ratio is a ratio of a maximum spectral amplitude with respect to a sum of other spectral amplitudes of the denoised first frequency domain information.

11. The respiration rate detection device as claimed in claim 9, wherein a relationship of a plurality of signal features with respect to a plurality of weightings is previously formed as a look-up table.

12. The respiration rate detection device as claimed in claim 9, wherein
the processor is built in with a plurality of respiration rate calculation algorithms, and
each of the set of respiration rate calculation algorithms is configured to respectively calculate a respiration rate component according to the filtered PPG signal.

13. The respiration rate detection device as claimed in claim 12, wherein the respiration rate is a sum of products of each of the set of weightings and the respiration rate component obtained by a corresponding respiration rate calculation algorithm among the set of respiration rate calculation algorithms.

14. The respiration rate detection device as claimed in claim 9, wherein
the processor is built in with a plurality of respiration rate calculation algorithms, and
the set of respiration rate calculation algorithms includes at least one of the plurality of respiration rate calculation algorithms.

15. The respiration rate detection device as claimed in claim 9, wherein
the processor is further configured to calculate a half of the reference index and a double of the reference index, and
the denoising parameter further comprises at least one of the half of the reference index and the double of the reference index.

16. A breath detection device, comprising:
an optical sensor configured to detect ejected light from the skin tissues in a detection period to generate a photoplethysmography (PPG) signal;
a motion sensor configured to output an acceleration signal corresponding to the detection period;
a band pass filter configured to filter the PPG signal and the acceleration signal; and
a processor configured to
respectively convert the filtered PPG signal and the filtered acceleration signal to first frequency domain information, which comprises a first frequency index set and a first spectrum value set associated with the first frequency index set, and second frequency domain information, which comprises a second frequency index set and a second spectrum value set associated with the second frequency index set,
identify a plurality of frequency indexes corresponding to a plurality of spectrum peak values in the first frequency domain information and the second frequency domain information,
determine a reference index as a denoising parameter according to a frequency index corresponding to a maximum spectrum peak value of the second frequency domain information to denoise the first frequency domain information by removing spectrum values, which correspond to frequency indexes of the denoising parameter, from the first frequency domain information to generate denoised first frequency domain information,
categorize the denoised first frequency domain information as one of a plurality of frequency zones according to predetermined categorization data, and
determine a breathing signal according to the denoised first frequency domain information within the categorized frequency zone.

17. The breath detection device as claimed in claim 16, wherein the processor is configured to
convert the denoised first frequency domain information to time domain to generate a denoised PPG signal, and
acquire a low frequency carrier of the denoised PPG signal as the breathing signal.

18. The breath detection device as claimed in claim 16, wherein the processor is configured to determine the breathing signal as a spectrum range in the first frequency domain information lower than 0.25 Hz.

* * * * *